United States Patent [19]
Wolf et al.

[11] Patent Number: 5,981,174
[45] Date of Patent: Nov. 9, 1999

[54] GENETIC ASSAY

[75] Inventors: Charles Roland Wolf, Perth; John Stephen Miles, West Bridgford; Nigel Kay Spurr, Bishops Stortford; Alan Charles Gough, Dorset, all of United Kingdom

[73] Assignee: Imperial Cancer Research Technology Limited, London, United Kingdom

[21] Appl. No.: 08/145,658

[22] Filed: Nov. 4, 1993

Related U.S. Application Data

[63] Continuation of application No. 07/732,223, Jul. 18, 1991, abandoned, which is a continuation-in-part of application No. PCT/GB91/00066, Jan. 17, 1991.

[30] Foreign Application Priority Data

Jan. 18, 1990 [GB] United Kingdom .................. 9001181

[51] Int. Cl.$^6$ .............................. C12Q 1/68; C07H 21/04
[52] U.S. Cl. .............................. 435/6; 435/91.2; 435/7.4; 536/24.3; 536/24.31; 536/24.33
[58] Field of Search .............................. 435/6, 91.1, 7.4, 435/91.2, 91.5; 536/23.1, 23.2, 23.5, 24.33, 24.3, 24.31

[56] References Cited

U.S. PATENT DOCUMENTS 5,648,482  7/1997  Meyer .................................. 536/24.33

FOREIGN PATENT DOCUMENTS 0 332 435  9/1989  European Pat. Off. .

OTHER PUBLICATIONS

Gough et al. "Identification of the Primary Gene Defect at the Cytochrome P450 CYP2D Locus" Nature, vol. 347, 25 Oct. 1990, pp. 773–776.
Gonzalez, Chemical Abstracts, 112:71647h (1990).
Heim et al., The Lancet, 336:529–532 (1990).
Skoda et al., PNAS, 85:5240–5243 (1988).
Saiki et al., Science, 293:487–491 (1988).
Kimura et al., Am. J. Hum. Genet., 45:889–904 (1989).
Gonzalez et al., Nature 331:442–446 (1988).
Gonzalez et al., Geomics, 2:174–179 (1988).
Manna et al., J. Clin. Invest, 83:1066–1072 (1989).
Miles et al., Nucleic Acids Research, vol. 17, No. 20:8241–8255 (1989).
Brosen et al., *Eur J. Clin Pharmacol*, 36:537–547 (1989).
Meyer et al., *The Lancet*, 336:889–890 (Oct. 6, 1990).
Turgeon et al., *Br. J Clin. Pharmac.*, 32:283–288 (1991).
Meyer et al., *Pharmac. Ther.*, 46:297–308 (1990).
Heim et al., *Genomics*, 14:49–58 (1992).

*Primary Examiner*—David Guzo
*Attorney, Agent, or Firm*—Dickstein Shapiro Morin & Oshinsky LLP

[57] ABSTRACT

Polymorphisms at positions 100, 271, 281, 294, 408, 506 or 1432 of the cytochrome P450 enzyme bufuralol-1'-hydroxylase are indicative of the extensive metaboliser/poor metaboliser phenotypes and can be detected using known methods such as amplification of the DNA with the polymerase chain reaction, followed by digestion with a suitable restriction enzyme and analysis by gel electrophoresis. The EM/PM phenotype is relevant to calculating safe or effective drug doses for individuals.

16 Claims, 18 Drawing Sheets

```
1                            30                              60
ATGGGGCTAGAAGCACTGGTGCCCCTGGCCGTGATAGTGGCCATCTTCCTGCTCCTGGTGGACCTGATGCACCGGCGCCA     db 1
................................................................................     pMP 33

90                          120                         150
ACGCTGGGCTGCACGCTACCCACCAGGCCCCCTGCCACTGCCCGGGCTGGGCAACCTGCTGCATGTGGACTTCCAGAACA     db 1
....................T...........................................................     pMP 33

170          ▽  1   A      210                         240
CACCATACTGCTTCGACCAG TGCGGCGCCGCTTCGGGGACGTGTTCAGCCTGCAGCTGGCCTGGACGCCGGTGGTCGTG     db 1
....................|GTTC........................................................     pMP 33

260     HhaI    SacII   HaoIII 300
CTCAATGGGCTGGCGGCCGTGCGCGAGGCGCTGGTGACCCACGGCGAGGACACCGCCGACCGCCCGCCTGTGCCCATCAC     db 1
...................A.........G............G.....................................     pMP 33

330       B    2    360                         390
CCAGATCCTGGGTTTCGGGCCGCGTTCCCAAG GGGTGTTCCTGGCGCGCTATGGGCCCGCGTGGCGCGAGCAGAGGCGCT     db 1
.................................................↑..............................     pMP 33/32

420                         450                 480
TCTCCGTGTCCACCTTGCGCAACTTGGGCCTGGGCAAGAAGTCGCTGGAGCAGTGGGTGACCGAGGAGGCCGCCTGCCTT     db 1
........C.........................................................................     pMP 33/32

3
        C    * 510                          540
TGTGCCGCCTTCGCCAACCACTCCG GACGCCCCTTTCGCCCCAACGGTCTCTTGGACAAAGCCGTGAGCAACGTGATCGC     db 1
............................|....................................................     pMP 33/32
..........G....AG...|.............................................................     'b'

570                         600                         630 **
CTCCCTCACCTGCGGGCGCCGCTTCGAGTACGACGACCCTCGCTTCCTCAGGCTGCTGGACCTAGCTCAGG-AGGGACTG     db 1
.......................................................................-..........     pMP 33/32
...........................................................................G.....TC.    'b'
```

FIG.2A

```
                          D
                    ────────────→
              660    4              690
     AAGGAGGAGTCGGGCTTTCTGCGCGAG|GTGCTGAATGCTGTCCCCGTCCTCCTGCATATCCCAGCGCTGGCTGGCAAGGT    db 1
     ..............................................................................    pMP 33/32
     ....................C.........|..........................C...C.................    'b'

720                 750                  780
     CCTACGCTTCCAAAAGGCTTTCCTGACCCAGCTGGATGAGCTGCTAACTGAGCACAGGATGACCTGGGACCCAGCCCAGC    db 1
     ..............................................................................    pMP 33/32
     ..............................................................................    'b'

810            840 ▽5            870
     CCCCCCGAGACCTGACTGAGGCCTTCCTGGCAGAGATGGAGAA|GCCAAGGGGAACCCTGAGAGCAGCTTCAATGATGAG    db 1
     ..............................................................................    pMP 33/32
     .A.....................A...A.........|................G.........................    'b'
                                       ↑
                        900                 930
     AACCTGCGCATAGTGGTGGCTGACCTGTTCTCTGCCGGGATGGTGACCACCTCGACCACGCTGGCCTGGGGCCTCCTGCT    db 1
     ..............................................................................    pMP 32
     ..............G.A........CT...............T....................................    'b'

▽6
     960                      **               1020
     CATGATCCTACATCCGGATGTGCA|-GCCCGTGTCCAACAGGAGATCGACGACGTGGATAGGGCAGGTGCGGCGACCAGAG    db 1
     ........................|-.....................................................    pMP 32
     ............C.T.........|T......................................................    'b'
                             --T.................................................      pMP 34

1050                1080                 1110
     ATGGGTGACCAGGCTCACATGCCCTACACCACTGCCGTGATTCATGAGGTGCAGCGCTTTGGGGACATCGTCCCCCTGGG    db 1
     ..............................................................................    pMP 32
     ............................................A...................................    'b'
     ...............................................C.............A........A.       pMP 34
```

FIG.2B

```
                    1140                          7    1180
      TATGACCCATATGACATCCCGTGACATCGAAGTACAGGGCTTCCGCATCCCTAAGGGAACGACACTCATCACCAACCTGT  db 1
      .G........................................................│..................... pMP 32
      .G........................................................│..................... 'b'
      .G........................................................│..................... pMP 34

1200                  1230                         1260
      CATCGGTGCTGAAGGATGAGGCCGTCTGGGAGAAGCCCTTCCGCTTCCACCCCGAACACTTCCTGGATGCCCAGGGCCAC  db 1
      ................................................................................ pMP 32
      ................................................................................ 'b'
      ..........................A..................................................... pMP 34

1290                   8      E                  1350
      TTTGTGAAGCCGGAGGCCTTCCTGCCTTTCTCAGCAGGCCGCCGTGCATGCCTCGGGGAGCCCCTGGCCCGCATGGAGCT  db 1
      ................................................................................ pMP 32
      ................................................................................ 'b'
      ................................................................................ pMP 34

1380                 HaeIII      1420         NcoI
      CTTCCTCTTCTTCACCTCCCTGCTGCAGCACTTCAGCTTCTCGGTGCCCACTGGACAGCCCCGGCCCAGCCACCATGGTG  db 1
      ................................................................................ pMP 32
      ..........................C...G..G.C.........................TC.C...           'b'
      ..........................C...G..G.C.........................TC.C...           pMP 34

1440         BstEII   1470                       1500
      TCTTT-GCTTTCCTGGTGAGCCCATCCCCCTATGAGCTTTGTGCTGTGCCCCGCTAGAATGGGGTACCTAGTCCCCAGCC  db1
      ......-...........C............................................................. pMP 32
      ..G.CA......-.....C............................................................. 'b'
      ..G.CA......-.....C..........C................................................. pMP 34

F
      TGCTCCTAGCCCAGAGGCTCTAATGTACAATAAAGCAATGTGGTAGTTCC(A)n                             db 1
      ......CTAG....................................                                    pMP 32
      ..........T...................................                                    'b'
      ......CTAG....................................                                    pMP 34
```

FIG.2C

EXON 2 PCR PRODUCT DIGESTION

```
1                        30                          60
ATGGGGCTAGAAGCACTGGTGCCCCTGGCCGTGATAGTGGCCATCTTCCTGCTCCTGGTGGACCTGATGCACCGGCGCCA    db1 (CYP2D6)
...........................A..................................A...                pMP33 (CYP2D6)
...........................A....C.........................G.A.A...                CYP2D7
.....G..T........................................................                 CYP2D8P 90                       120                      150
ACGCTGGGCTGCACGCTACCACCAGGCCCCCTGCACTGCCCGGCTGGGCAACCT-GCTGCATGTGGACTTCCAGAACA    db1 (CYP2D6)
.................T..........................................T.........            pMP33 (CYP2D6)
............G....T..........................................T..-                  CYP2D7
............A....G...........................................T..-                 CYP2D8P 170                       210                      240
CACCATACTGCTTCGACCAGTTGCGGCGCCGCTTCGGGGACGTGTTCAGCCTGCAGCTGGCCTGGACGCCGGTGGTCGTG    db1 (CYP2D6)
....................|GTTC...........................................T..........   pMP33 (CYP2D6)
.............C......|........................T.....................               CYP2D7
---T.....AC....A....|........A.................................                    CYP2D8P
              260

300
CTCAATGGGCTGGCGGCCGTGCGCGAGGCGCTGGTGACCCACGGCGAGGACACCGCCGACCGCCCCGCCCTGTGCCCATCAC    db1 (CYP2D6)
..................A...................G...........................                pMP33 (CYP2D6)
..................A...................G.........................C........TA       CYP2D7
...............T..TG..................G..........................C........TA      CYP2D8P
```

FIG.7A

```
                    330                     2       360                                   390
CCAGATCCTGGGTTTCGGGGCGCGTTCCCAAGGGGTGTTCCTGGCGCGCTATGGGCCCGCGTGGCGGGAGCAGAGGCGCT    db1 (CYP2D6)
..............G.........................................................         pMP33/32 (CYP2D6)
..............G........C.........................T.............................   CYP2D7
..............G.......CA........................................................   CYP2D8P 420                             450                                   480
TCTCCGTGTCCACCTTGCGCAACTTGGGCCTGGGCAAGAAGTCGCTGGAGCAGTGGGTGACCGAGGAGGCCGCCTGCCTT    db1 (CYP2D6)
.......C.........................................................................   pMP33/32 (CYP2D6)
..................................................C.............................   CYP2D7
.................................................G.............................C   CYP2D8P 3    510                      540
TGTGCCGCCTTCGCCAACCACTCCGGACGCCCCTTTCGCCCCAAGGTCTCTTGGACAAAGCCGTGAGCAACGTGATCGC     db1 (CYP2D6)
...G....AG......CG.....................................................           pMP33/32 (CYP2D6)
...G....AG..............A.............C..C..A........G.C.                         "b" (CYP2D9)
...G....AG..A                                                                       CYP2D7
                                                                                    CYP2D8P
```

FIG. 7B

```
       570                  600                      630
CTCCCTCACCTGCGGGGCGCCGCTTCGAGTACGACGACCCTCGCTTCCTCAGGCTGCTGGACCTAGCTCAGG-AGGGACTG   db1 (CYP2D6)
..............................................................(G)....TC.          pMP33/32 (CYP2D6)
.........T..........................................A.............               'b' (CYP2D9)
..........................................................A-.......T.             CYP2D7
                                                                                    CYP2D8P 660                  690                      720
AAGGAGGAGTCGGGCTTTCTGCGCGAGGTGCTGAATGCTGTCCCGTCCTCCTGCATATCCCAGCGCTGGCTGGCAAGGT    db1 (CYP2D6)
.........................................................(C).C.............      pMP33/32 (CYP2D6)
.............C............A....T....C.......                                       'b' (CYP2D9)
.............C............A..........C...GC......G..........                       CYP2D7
........CT...........T.A..A.A..                                                    CYP2D8P 720                  750                      780
CCTACGCTTCCAAAAGGCTTTCCTGACCCAGCTGGATGAGCTGCTAACTGAGCACAGGATGACCTGGACCCAGCCAGC    db1 (CYP2D6)
.............................................................................    pMP33/32 (CYP2D6)
.............................................................................    'b' (CYP2D9)
........................................G..C............A....T...........       CYP2D7
..C..........................................................T...........       CYP2D8P
```

```
                    1050                      1080                      1110
ATGGGTGACCAGGCTCACATGCCCTACACCACTGCCGTGATTCATGAGGTGCAGCGCTTTGGGGACATCGTCCCCCTGGG    db1 (CYP2D6)
................................................................................    pMP32 (CYP2D6)
.........................................(A).................................A.    'b' (CYP2D9)
..........................................C..................A................    pMP34 (CYP2D7)
..........................................C..................A...............A.    CYP2D7
.......................G.........G........C..................A................    CYP2D8P 1140                    7 1180
TATGACCCATATGACATCGAAGTACAGGGCTTCCGCATCCCTAAGGAACGACACTCATCACCAACCTGT    db1 (CYP2D6)
...................................................................    pMP32 (CYP2D6)
...................................................................    'b' (CYP2D9)
.G.................................................................    pMP34 (CYP2D7)
.G.............A...................................................    CYP2D7
.G.................................................T-.TG..T........    CYP2D8P 1200                     1230                     1260
CATCGGTGCTGAAGGATGAGGCCGTCTGGGAGAAGCCCTTCCGCTTCCACCCGAACACTTCCTGGATGCCCAGGGCCAC    db1 (CYP2D6)
...............................................................................    pMP32 (CYP2D6)
...............................................A..............................    'b' (CYP2D9)
...............................................A..............................    pMP34 (CYP2D7)
...............................................A..............................    CYP2D7
...............................................................................    CYP2D8P
```

FIG. 7E

```
                                                                        1350
1290                       8
TTTGTGAAGCCGGAGGCCTTCCTGCCTTTCTCAGCAG CCCCGTGCAT GCTCGGGG-AGCCCCTGCCCGCATGGAGCT    db1 (CYP2D6)
....................................   .........  ..........-...................    pMP32 (CYP2D6)
....................................   .........  ..........-...................    'b' (CYP2D9)
....................................   .........  ..........-...................    pMP34 (CYP2D7)
....................................   .........  ..........-...................    CYP2D7
....................................   .........  .........CC........A........    CYP2D8P 1420
                1380
CTTCCTCTTCTTCACCTCCCTGCTGCAGCACTTCAGCTTCTCGGTGCCCACTGGACAGCCCCGGCCCAGCCACCATGGTG    db1 (CYP2D6)
...........................................................................TC.C...    pMP32 (CYP2D6)
...........C...G..G..C.....................................................TC.C...    'b' (CYP2D9)
...........C...G..G..C.....................................................TC.C...    pMP34 (CYP2D7)
...........C...G..G..C.....................................................TC.C...    CYP2D7
...........C...............................................C..............TC.C...    CYP2D8P
```

GENETIC ASSAY

This is a continuation, of application Ser. No. 7/732,223, filed Jul. 18, 1991, now abandoned, which is a continuation-in-part application of international application PCT/GB91/00066, filed on Jan. 17, 1991, which designated the United States.

FIELD OF THE INVENTION

The present invention relates to a genetic assay, that is to say an assay which reveals the presence or absence of a genetic characteristic.

It is known that mutations in regions of the nucleic acids of organisms can alter the nature or amount of polypeptides encoded by such regions or encoded by other regions associated with the site of mutation.

We have now found several sites of mutation in mammalian DNA associated with the cytochrome P450-dependent monooxygenase supergene family of enzymes. The presence or absence of mutation at one or more of these sites has been found to indicate with a high degree of certainty whether the individual is an "extensive metaboliser" or a "poor metaboliser".

REFERENCES

Several publications are referenced herein by Arabic numerals within parentheses. Full citations for these references may be found at the end of the specification immediately preceding the claims. The disclosures of these publications are hereby incorporated herein by reference in their entirety, unless otherwise noted.

BACKGROUND OF THE INVENTION

Skoda et al (1988 *P.N.A.S.* 85, 5240–5243) disclosed an RFLP-based assay which identifies only about 25% of poor metabolisers.

Cytochrome P450-dependent monooxygenases (P450s) are a supergene family of enzymes that catalyse the oxidation of lipophilic chemicals through the insertion of one atom of molecular oxygen into the substrate. They are involved in the metabolism of xenobiotic compounds, and in particular with the clearance of at least 25 drugs, including debrisoquine, sparteine, bufuralol and dextromethorphan. Other drugs whose metabolism is related to the debrisoquine oxidation polymorphism (as of June 1990) include (in the cardiovascular area) metoprolol, timolol, propranolol, perhexilene, N-propylamaline, propafenone, encainide, flecainide and mexiletine, (in the psychiatric area) amitriptyline, imipramine, desipramine, nortriptyline, clomipramine, thioridazine, perphenazine, amiflamine and tomoxitene and (in other areas) codeine, methoxyphenamine and phenformin and possibly also chlorpropamine, melatonin and MPTP. The P450 system is polymorphic in man, and genetic differences in the P450-mediated metabolism of a wide variety of drugs have been clearly demonstrated. The best example of this is the debrisoquine/sparteine polymorphism, (see Ref 1 for a review). Up to 10% of the Caucasian population exhibit the poor metaboliser (PM) phenotype. This is characterised by a significantly reduced ability to metabolise the prototype drug debrisoquine to 4-hydroxydebrisoquine, the metabolism being 10–200 times less than in extensive metabolisers (EMs). The PM phenotype is inherited as an autosomal recessive trait, and up to 54% of people are carriers of a mutant allele(s). The PM phenotype leads to impaired clearance of over twenty other commonly prescribed drugs and may result in serious adverse side effects upon their administration. Thus the ability to predict phenotype is an attractive possibility which would be useful in many clinical situations.

Recently the cytochrome P450 isozyme (P450 db1, also called P450 buf 1 or P450 DB) responsible for the metabolism of debrisoquine, sparteine and other compounds related to the polymorphism has been purified from human liver. Immunoquantitation of this protein correlates well with the levels of bufuralol-1'-hydroxylase activity in a series of human livers, bufuralol being a prototype substrate for the db1 isozyme. Furthermore no immuno-reactive db1 protein was detected in liver microsomes of PMs suggesting that the complete or almost complete absence of this protein leads to the PM phenotype. Recent work also provides evidence for the presence of allozymes of P450db1 with altered $K_m$ and $V_{max}$ probably due to amino acid substitutions. Antibodies against human P450db1 have been found in patients with autoimmune hepatitis type II but the relationship between the debrisoquine polymorphism and the appearance of these autoantibodies is not known.

Gonzalez and coworkers have isolated cDNA clones from libraries made from the livers of EMs and have shown that they encode active P450db1 by expression in COS-1 cells and measurement of bufuralol-1'-hydroxylase activity (2). Sequence analysis shows that P450 db1 belongs to a distinct P450 subfamily, P450IID (3). P450IID cDNA clones were also obtained from libraries made from the livers of PMs and in these cases they appeared to be derived from aberrantly or incompletely spliced mRNAs, and therefore would not be able to encode an active P450db1. Four variants were described: "a" which retains intron 5; "b" which retains intron 6; "b'" which has lost the 3' half of exon 6 in combination with the removal of intron 6; and another cDNA clone from a PM liver, variant "c", which appears to be normally spliced but has several base substitutions and was not characterised further. It was inferred from these studies that the defective mRNAs (cDNAs) were the products of mutant alleles of the P450db1 gene.

The gene encoding P450db1 (CYP2D1) has been located on chromosome 22 and Southern blot analysis shows that there is probably more than one gene/pseudogene within the CYP2D locus based on the amount of DNA hybridizing to the db1 cDNA probe. The CYP2D locus is highly polymorphic, and two alleles, detected using the restriction enzyme XbaI, have been associated with the PM phenotype (44 kb allele and 11.5 kb allele; 4). However, at the present time these restriction fragment length polymorphisms (RFLPS) are not informative in predicting phenotype as they do not identify all PM individuals (4).

SUMMARY OF THE INVENTION

We have now cloned and sequenced further novel P450IID cDNAs, none of which we predict would encode an active P450. By comparison with the available P450IID cDNA sequences, we have identified base-pair differences which form the basis of a genotyping assay for the PM phenotype.

One aspect of the invention provides a method of detecting a mutation at positions 100, 271, 281, 294, 408, 506 or 1432 of the DNA sequence of P450IID bufuralol-1'-hydroxylase or a deletion of at least part of exon 9 thereof.

The enzyme is also called debrisoquine hydroxylase and P450IID6 and is encoded by gene CYP2D6.

In the case of positions 100, 271, 281, 294, 408 and 1432, the mutation is typically one or more base pair substitutions such as C→T, C→A, A→G, C→G, G→C or C→T respectively. (These alterations are more fully written as cytosine to thymidine, cytosine to adenosine, adenosine to guanine, cytosine to guanine, guanine to cytosine and cytosine to thymidine.) In the case of a polymorphism at position 506, the mutation is typically a base pair deletion in the spliced product, resulting, apparently, from a G→A transition in the last nucleotide of intron 3. Since the assay will normally be directed to genomic DNA, it is the G→A transition which is detected directly.

The mutations at positions 100, 271, 281 and 294 are either silent or lead to single amino acid substitutions. In themselves, they do not account for the PM phenotype but they are strongly linked with the base pair deletion at 506 and are therefore informative.

The assay may involve any suitable method for identifying such polymorphisms, such as: sequencing of the DNA at one or more of the relevant positions; differential hybridisation of an oligonucleotide probe designed to hybridise at the relevant positions of either the wild-type or mutant sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for the EM sequence and unmatched for the PM sequence or vice versa; or the selective introduction of a restriction site using a PCR (or similar) primer matched for the PM or EM genotype, followed by a restriction digest. The assay may be indirect, ie capable of detecting a mutation at another position or gene which is known to be linked to one or more of the positions listed above, especially the deletion at position 506. Assays directed to the related locus CYP2D7 may be used in this way. A number of sites in the "b" variant sequence (Gonzalez et al) have recently been analysed and also been shown to be informative for the PM phenotype. The "b" variant appears to be derived from a gene other than the P450IID6 but its presence is tightly linked to the PM phenotype and the presence of the "a" variant. Base pair differences between the "b" variant and other genes in this cluster which may be used as a basis for a genotyping assay include for example, bp 632 (G insertion); bp 637 and 638 (TC to CT); bp 691 (C to T); bp 832 (A to G); bp 1085 (T insertion); 1094 (G to A); bp 1528 (T to C). The probes and primers may be fragments of DNA isolated from nature or may be synthetic.

A non-denaturing gel may be used to detect differing lengths of fragments resulting from digestion with an appropriate restriction enzyme. The DNA is usually amplified before digestion, for example using the polymerase chain reaction (PCR) method disclosed in reference 5 and modifications thereof. Otherwise 10–100 times more DNA would need to be obtained in the first place, and even then the assay would work only if the restriction enzyme cuts DNA infrequently.

Amplification of DNA may be achieved by the established PCR method or by developments thereof or alternatives such as the ligase chain reaction, QB replicase and nucleic acid sequence-based amplification.

An "appropriate restriction enzyme" is one which will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. Various enzymes are disclosed below as specific examples, but any enzyme which cuts at the same place (an "isoschizomer") or which recognises the same sequence and cuts the DNA at a point within or adjacent the sequence will be suitable; more are being discovered all the time. It is convenient if the enzyme cuts DNA only infrequently, in other words if it recognises a sequence which occurs only rarely.

Restriction enzymes useful in connection with the mutations described above include, for example, HaeIII for position 294, SacII for 281, HhaI for 271, EcoRI for 408, BstNI for 506 and ApyI for 100. These enzymes are available commercially from suppliers of biological reagents, such as BRL-Gibco, Paisley, Scotland.

In another method, a pair of PCR primers are used which match (ie hybridise to) either the PM genotype or the EM genotype but not both. Whether amplified DNA is produced will then indicate the PM or EM genotype (and hence phenotype). However, this method relies partly on a negative result (ie the absence of amplified DNA) which could be due to a technical failure. It is therefore less reliable and/or requires additional control experiments.

A preferable method employs similar PCR primers but, as well as hybridising to only one of the PM or EM sequences, they introduce a restriction site which is not otherwise there in either the PM or EM sequences. For example, PCR primers G and H:

(G) 5'-GATGAGCTGCTAACTGAGCCC-3' (SEQ ID NO:5)

(H) 5'-CCGAGAGCATACTCGGGAC-3' (SEQ ID NO:6)

will introduce a MspI site at the 775 region in the PM sequence. Neither the PM nor EM sequences have a MspI site at that position. Thus, in a single two-step process of PCR amplification with primers D, C, G and H followed by a restriction digest with BstNI and MspI, both mutations can be detected.

In a further embodiment, a large deletion encompassing the whole CYP2D6 gene (the deletion being present in about 10% of mutant alleles) is detected by using any pcr primer specific for the CYP2D6 gene so that no amplification occurs when the gene is deleted. A suitable primer is:

(J) 5'-TGCCGCCTTCGCCAACCACT-3' (SEQ ID NO:9)

In a still further embodiment, a base deletion at position 2637 in exon 5 (Heim & Mayer (1990) Lancet, 336 529, incorporated herein by reference) which results in a premature stop codon and which is present in about 1–5% of mutant alleles, is detected by using site-directed mutagenesis, for example, using the mismatched oligonucleotide PCR primer (K) 5'-GGCTGGGTCCGAGGTCACCC-3' (SEQ ID NO:10)

to introduce a restriction site specifically into the wild-type or the mutant allele, but not both.

In these approaches the base pair difference between the normal and mutant allele, in combination with an additional base pair inserted into the PCR product with the mismatched oligonucleotide, introduces a restriction site only present in the normal allele (see later).

Previously, the analysis of two or more mutant alleles has required the use of several allele specific primers and the need for multiple PCR reactions. Combining the strategies described above the close proximity of the mutations in the CYP2D6 gene allows the analysis of all the known mutant alleles using one PCR reaction. Gene specific primers are needed because of the presence of more than one highly homologous gene in the CYP2D gene cluster.

The nucleic acid, usually genomic DNA rather than RNA, which is assayed may be obtained from any cell of the body (such as hair roots, buccal epithelial cells and blood spots) or even urinary deposits. Conveniently, a mouthwash or drop of blood is taken, either of which will contain a few cells. Preferably, the DNA is extracted by known techniques and a specific region of the P450IID sequence is amplified using the PCR. It is then digested with the restriction enzyme and subjected to PAGE (polyacrylamide gel electrophoresis). The gel is stained and photographed to reveal a pattern of fragments indicative of whether the patient is homozygous EM/EM, homozygous PM/PM or heterozygous. The whole procedure, using current technology, takes about 5 hours whereas existing methods in which drug metabolism is monitored take up to 3 days and are much more difficult to perform.

A kit may be provided, according to another aspect of the invention, to perform the assay. The kit will typically contain the primer(s) needed for the PCR amplification (if PCR amplification is used) and also control DNA for both homozygotes and the heterozygote, so that the results of the assay can be analysed more readily. Conveniently, the kit also comprises the restriction enzyme(s) and, preferably, phenol and SDS (sodium dodecyl sulphate) or similar materials used in the mouthwash.

The assays of the invention will be extremely valuable in relation to human medicine and may be used prior to treatment with a drug which is toxic if not metabolised or which is effective only if metabolised. They may al so be used to identify individuals who are genetically predisposed to be susceptible to or resistant to diseases the etiology of which is linked to the PM/EM phenotype, for example lung and bladder cancer. The mutations described above are known to occur in European Caucasians and may or may not be present in other races such as Mongoloids and Negroids.

It is entirely possible that other mutations will be found which indicate the PM phenotype. If so, the assays of the invention may be used together with assays for such other mutations in order to provide a definitive PM/EM phenotyping assay.

The assays of the invention may be used as part of the clinical trials of a new drug: by phenotyping the healthy volunteers or patients in the trials and conducting appropriate drug metabolism studies, it can be established whether the drug's metabolism is affected by the PM/EM phenotype.

Examples of the invention will now be described with reference to the accompanying drawings, the legends for which are as follows:

BRIEF DESCRIPTION OF THE DRAWINGS

FIG. 2 (on three sheets: FIG. 2A, FIG. 2B, and FIG. 2C): This shows a comparison of nucleotide sequences of DNA encoding functional debrisoquine hydroxylase (db1) and related cDNAs (SEQ ID NO:13, 20, 21 and 22). The sequences for db1 and variant "b" are taken from Gonzalez et al (2). Numbering starts at the initiation codon for db1. The variant "a" cDNA sequence was compiled from two cDNAs, pMP32 and pMP33 which contained an identical sequence over an overlapping region of 462 bp. This sequence contained only one base-pair difference to the partial sequence described as variant "a" by Gonzalez et al (G to C at position 383) which covers the region 299–1567 bp. The base-pair deletion at position 506 is marked *. The position of introns (vertical lines) is obtained from the sequence of P45011D6 gene (11). Triangles represent the positions of intron sequences in the isolated variant cDNAs: 1. The first 64-bp of intron 1 in pMP33; 5. Insertion of intron 5 in the variant "a" cDNA described by Gonzalez et al but which was absent from pMP32 and pMP33; 6. Insertion of part of intron 6 in both pMP34 and variant "b". The position of the bp insertions (G) at position 631 and at 983 (T) in the "b" variant are shown **. The positions of oligonucleotide primers used to amplify specific regions of the genes are marked by capital letters and horizontal arrows. The oligonucleotide marked D was taken from the sequence of intron 4 (see FIG. 5). The diagnostic restriction sites used to differentiate between either db1 (variant "a") and variant "b" or db1 and variant "a" are marked.

FIG. 7: This shows the "b" variant sequence and others alongside the db1 sequence (SEQ ID NO:13, 20, 21, 22 and 23), with the region around exon 7 shown in more detail in FIG. 8. Sites on SEQ ID NO:14, 15, 16, 17, 18 and 19 cut by restriction enzymes HaeIII, DraIII and HhaI are shown as A, B and C respectively. HaeIII cuts db1 only. DraIII cuts 2D7 (pMP34) and 2d8 sequences only at 1083. A combination of HaeIII and DraIII is useful but inconvenient. A HhaI site is absent in the "b" variant at 1094 but present in all other variants so far found. Primer pair 1+2 is used for HaeIII/DraIII analysis and 3+2 for HhaI/DraIII analysis.

FIG. 10: Shows banding patterns diagnostic for PM's and heterozygotes at the CYP2D6 gene locus.

FIG. 10(a) is a diagrammatic representation of cleavage sites in the CYP2D6 PCR product showing the origin of the restriction fragments, whereas

MATERIAL & METHODS

Figure 1:
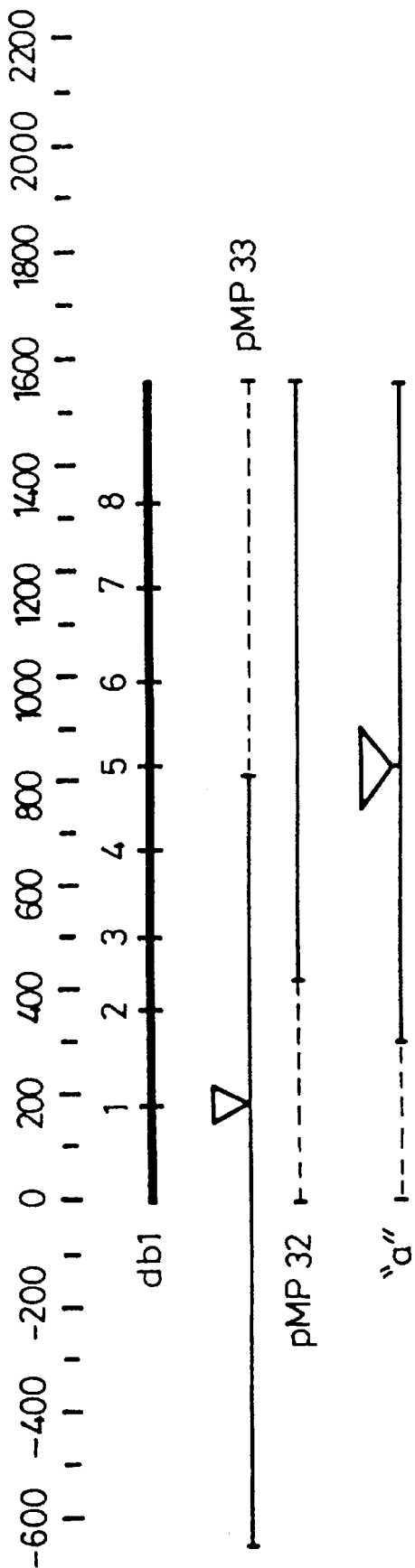
FIG. 1: This is a diagrammatic representation of the db1-related cDNA clones aligned with db1. Clones pXP32 and pMP33 are from this work, and db1 and "a" taken from Gonzalez et al (2). The numbering refers to that for db1 starting at the initiation codon. The positions of the introns, inferred from comparison with other P450II genes, are indicated on db1 by vertical lines, and the retention of part of intron 1 (pMP33) and intron 5 ("a") is indicated by triangles. Base pair substitutions and other differences between the cDNA sequences are given in full in FIG. 2. The dashes represent sequence not present in the variant cDNAs compared to db1.

Preparation of radioactive probes. The human P450 db1 (P450IID1; 2) cDNA probe was kindly provided by Drs. F. J. Gonzalez and U. A. Meyer. Restriction fragments for use as probes were isolated from low gelling temperature agarose and radioactively labeled with [$\alpha$-$^{32}$P]dCTP (3000 Ci mmol$^{-1}$; Amersham International) by random primer extension (6). Oligonucleotides were made on an Applied Biosystems 380A machine and labeled with [$\alpha$-$^{32}$P]ATP (3000 Ci mmol$^{-1}$; Amersham International) and T4 polynucleotide kinase.

Isolation of human P450IID-related cDNA clones. The full length P450IID6 (db1) cDNA was used to screen plaques from two human liver lambda gt11 cDNA libraries (Clontech, Palo Alto, Calif.; and Kwok et al [7]) made from individuals of unknown phenotype. Two different cDNA clones, lambda MPA (1.22 kb) and lambda MPG (1.56 kb) from the Clontech library were subcloned into pUC18 to give pMP32 and pMP33 respectively, and also into M13mp18 for sequence analysis.

DNA sequence analysis. The dideoxy chain termination method was used with [$\alpha$-$^{35}$S] thio DATP (400 Ci mmol$^{-1}$; Amersham International) to sequence DNA cloned in M13 (8, 9). Overlapping sequences were derived using a series of synthetic oligo-nucleotides and both DNA strands were fully sequenced. Sequences were compiled and analysed using Staden Plus software implemented on a DCS286 computer (10). DNA sequences generated during the course of this work have been deposited in the EMBL Data Bank with accession nos. X16865 and X16866.

Phenotyping. Individuals GT, MJ, TR, PJ and ML were phenotyped in vivo by Prof. G. Tucker, Department of Pharmacology and Therapeutics, University of Sheffield, U.K. using debrisoquine; and individuals A, 1.1, 2.2, and 3.3 were phenotyped using sparteine in vivo by us. Post-mortem liver samples E4, E6, E8 and E11 were phenotyped in vitro by Dr. U. A. Meyer, Biozentrum, Basel using bufuralol, and LVII showed no cross-reactivity with a monoclonal antibody raised against rat P450db1 (kindly supplied by Dr Meyer).

DNA amplification. Total DNA was isolated from blood lymphocytes or from liver using an Applied Biosystems 340A nucleic acids extractor according to the manufacturer's instructions. Target DNA (1 $\mu$g for genomic DNA or 1 ng for cloned cDNA) was used in the polymerase chain reaction (PCR; 5) with 600 ng of each amplification primer. The PCR was carried out using 2.5U Taq DNA polymerase (Cetus Corporation) according to the manufacturer's conditions except that dimethyl sulphoxide was added to 10% (v/v) final concentration. The chain reaction was initiated by denaturing DNA at 92° C. for 1 min, annealing by cooling to 60° C. for 1 min and extending at 72° C. for 2 min; twenty cycles were performed using either a Cetus or Techne programmable heating block. Pairs of oligonucleotide primers enabling the amplification of specific exon sequences were used as described in the legend to FIG. 2.

Analysis of amplified DNA. The products of DNA amplification (between 1/20–1/10 of the total) were either left uncut or digested with diagnostic restriction enzymes and separated electrophoretically on 6% polyacrylamide gels. In some cases the DNA was analysed by Southern blotting. Briefly, the DNA was transferred to Hybond N by alkali transfer (1.5M NaCl, 0.25M NaOH) and baked at 80° C. for 2 h. Membranes to be probed with cDNAs were pre-hybridised at 65° C. in 5×SSC, 4× Denhardt's, 10% SDS, 0.1% NaPPi, 20 $\mu$g ml$^{-1}$ salmon sperm DNA. Hybridisation was overnight in the same buffer except no salmon sperm DNA was present. Filters were washed to a final stringency of 0.2× SSC, 0.1% SDS, 0.1% NaPPi at 65° C. Oligonucleotide probes covering the region of interest were hybridised to the membranes at 37° C. in 6× SSC, 0.1% NaPPi and washed in the same buffer at a temperature dependent on their $T_m$. Membranes were exposed to Kodak XAR-5 film for between 2 h and three days at −80° C.

EXAMPLE 2

Comparison of db1-related DNA sequences

The nucleotide sequences derived from pMP32 and pMP33 were compared with the sequences of the db1 cDNA (encoding a functional P450 with bufuralol 1'-hydroxylase activity) as well as the variant "a" cDNA described by Gonzalez et al (2) and amended in the EMBL Data Bank; accession no. Y00300 (FIGS. 1 & 2). The sequences of pMP32 and pMP33 have an identical sequence over an overlapping region of 445 bp. Together these clones constitute a full length cDNA. However, we did not expect the sequence generated by pMP32/pMP33 to encode a functional protein as it contains part of intron 1 and perhaps more importantly a single base deletion at position 506 which would lead to a frame-shift (FIG. 2). Variant "a" of Gonzalez et al (2) also contains this same frame-shift and so with or without the retention of intron 5 or intron 1 this variant would not encode a functional protein (FIG. 2). Analysis of the genomic P450II2D sequence showed that the bp deletion at position 506 is due to a G to A transition at the junction of intron 3 and exon 4. This mutation removes a BstNl site in the gene compared to db1.

There are a significant number of base pair differences between the sequence of pMP32/pMP33, representing a full length variant, non-functional db1 sequence, and the normal db1 sequence. All of these differences may serve as markers for the PM phenotype and may therefore be of use in a genotyping assay.

EXAMPLE 3

Analysis at position 294

Figure 3:
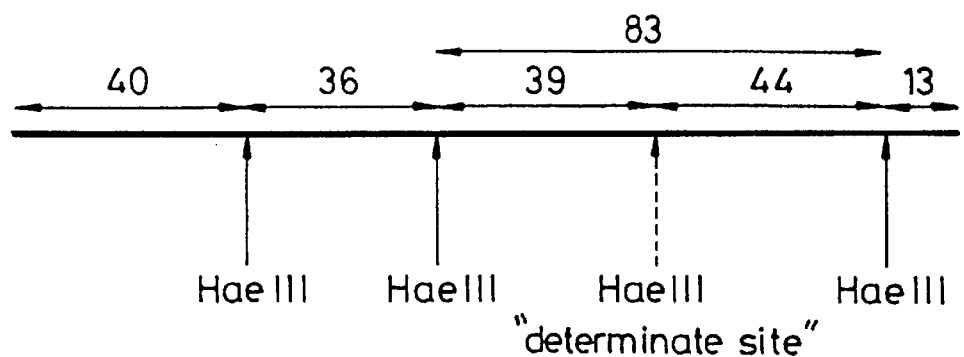
FIG. 3: This is a schematic illustration of HaeIII cleavage sites in the PCR fragment generated from the db1 gene using oligonucleotides A and B as primers (see FIG. 2). The location of the determinative HaeIII site when position 294 is mutated is shown. The fragment generated is 172 bp in length and incorporates the sequences of intron 1 and exon 2.
Figure 4:
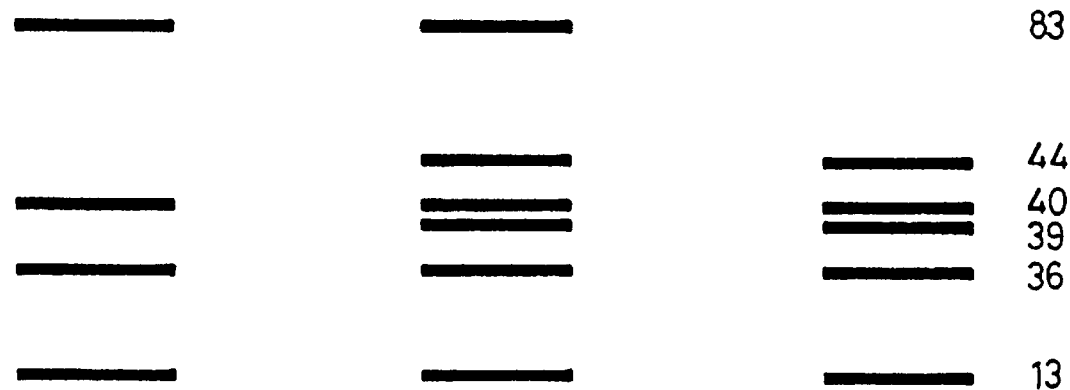
FIG. 4: This is a schematic illustration of the DNA fragmentation pattern obtained following polyacrylamide gel electrophoresis of the HaeIII-cleaved exon 2 DNA shown in FIG. 3 for both homozygote EM, homozygote PM and heterozygote individuals.

An analysis at position 294 is shown as an example in FIGS. 3 and 4. DNA covering the region of interest was amplified by PCR from genomic DNA using the oligonucleotides A and B (FIG. 2). This generates a DNA fragment of 172 bp in length (FIG. 3). In PM individuals the 83 bp fragment generated by digestion with the restriction enzyme HaeIII will cut into two pieces (39 and 44 bp) due to the HaeIII site generated by the mutation at position 294. In homozygous EM's this site is absent. 100% agreement between phenotype, assessed by measuring the rate of metabolism and marker drugs, and genotype was observed in the 16 individuals tested, with the gels corresponding to the expected appearance shown in FIG. 4.

Analysis of a region of exon 9 using oligonucleotide primers E and F (see FIG. 2) showed that in some PM individuals no db1 related band could be observed, indicating a deletion of this region of the gene. This also is informative for the PM phenotype in some individuals.

EXAMPLE 4

Analysis at position 506

Genomic DNA from individuals phenotyped either as poor or normal metabolizers was amplified by PCR using an oligonucleotide derived from exon 3 and one derived from intron 4 (marked C and D in FIG. 2) using an annealing temperature of 60° C. The sequence of oligonucleotide D was AAATCCTGCTCTTCCGAGGC (SEQ ID NO:4). The use of this oligonucleotide pair and the high annealing temperature assured specificity for the P450IID6 gene. The resulting fragment of 334 bp was then digested with the restriction enzyme BstNI and the products separated on an 8% polyacrylamide gel. Bands were visualized by ultraviolet irradiation of the gel stained with ethidium bromide.

Figure 5:
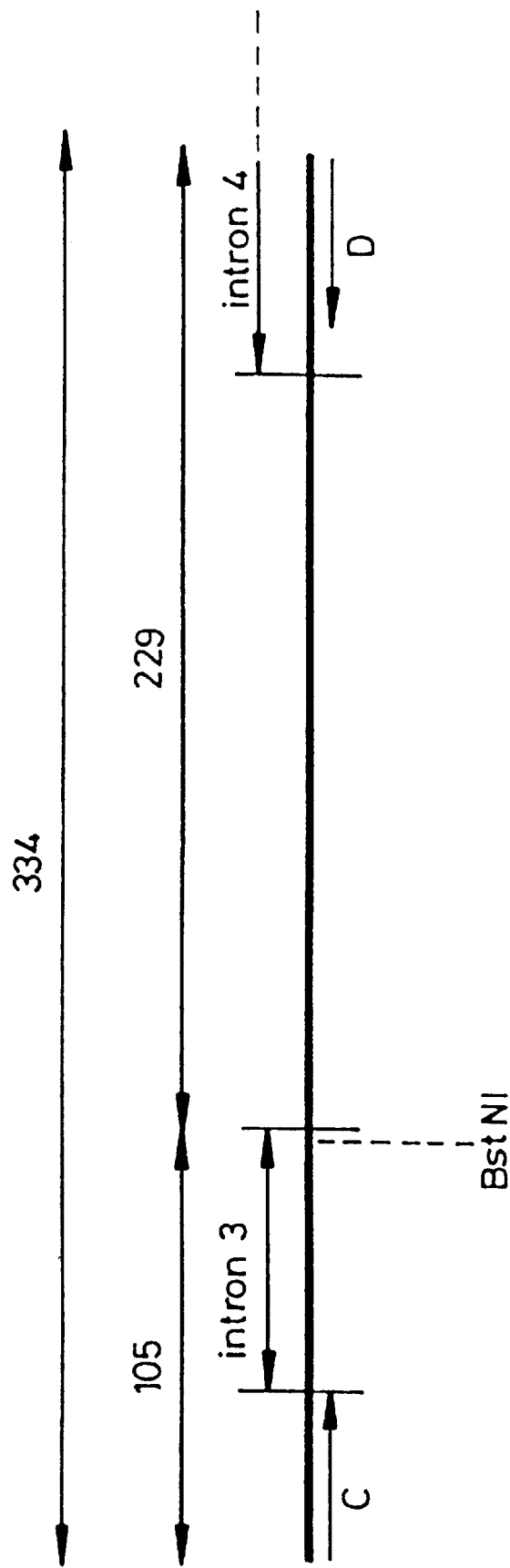
FIGS. 5 & 6: Analysis of the mutation site leading to the base-pair deletion in db1 cDNA at position 506. Diagrammatic representation of the method used and (FIG. 6) predicted banding pattern for individuals containing the db1 gene, variant "a" or both. Amplification of DNA from exon 3 into intron 4 produced a 334-bp fragment which in individuals containing the db1 sequence digests into fragments of 105 bp and 229 bp with BstNI. The variant "a" sequence (PM's) is resistant to digestion with this enzyme.
Figure 6:
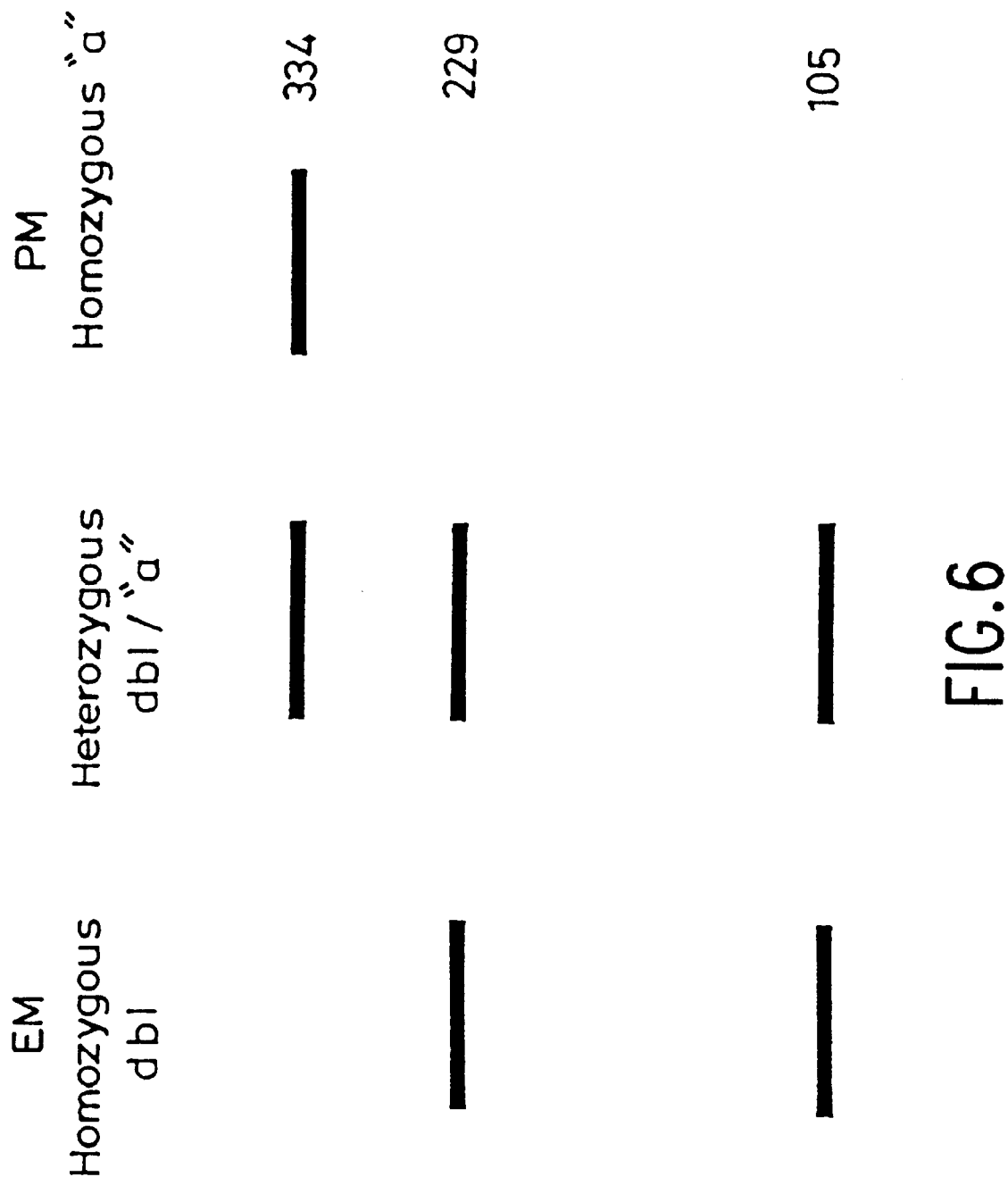
Figure 8:
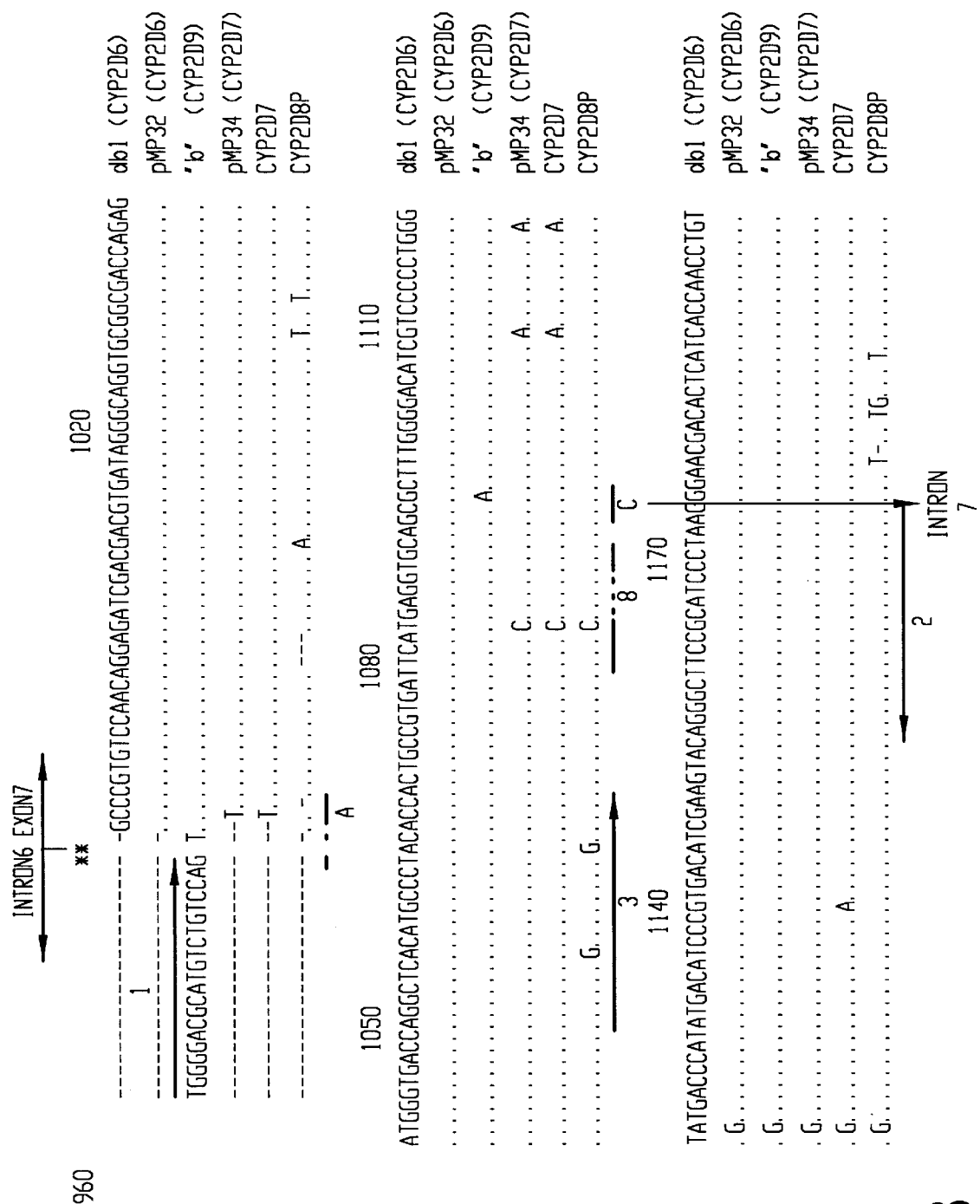

FIGS. 5 and 6 show the rationale and (schematically) the results.

Examination of the db1 sequence over the intron 3-exon 4 junction suggests two explanations for the base-pair (G) deletion in the cDNA sequences. The db1 intron 3-exon 4 junction has the sequence CCCCCAG/GACGCC (SEQ ID NO:25) (the bold letters indicate the start of exon 4)[19]. Therefore, either a base-pair (G) deletion to give CCCCCAG/ACGCC, or a G to A transition to give the sequence CCCCCAAG/ACGCC, which shifts the position of the 3' splice site, will result in the loss of the first base (G) in exon 4. In both cases the BstNI restriction site is lost. To establish which was the case we sequenced the PCR amplification product from 20 affected individuals. In all of these the G to A transition was shown to be the mutation responsible for the poor metabolizer phenotype. This transition appears to be the primary defect responsible for the poor metabolizer phenotype. Over 80% of individuals tested were homozygous for the G to A transition. Interestingly, individuals with this mutation were the same as those with the mutations at position 100 and in exon 2.

EXAMPLE 5

Figure 7D:
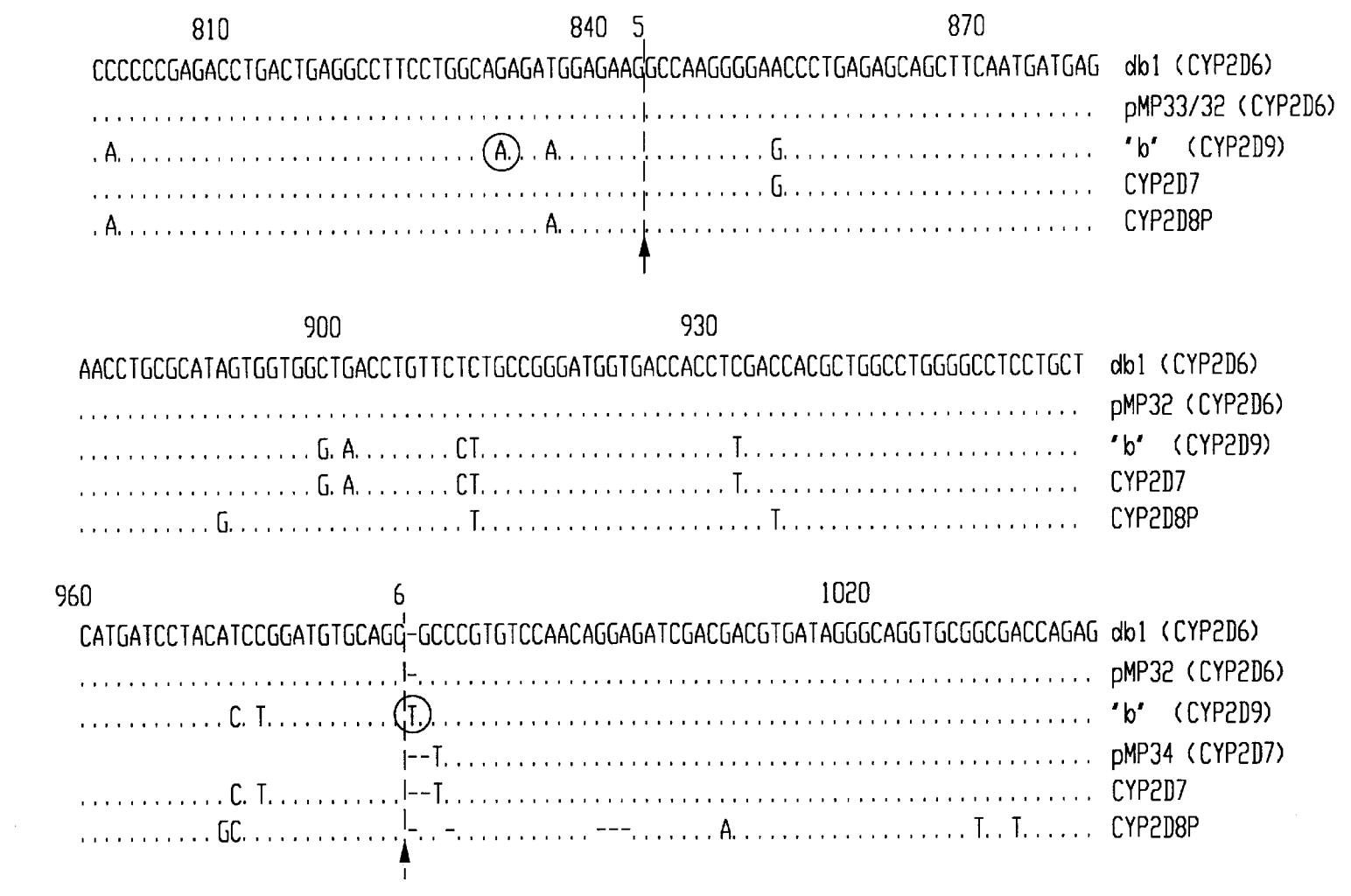
Figure 7G:
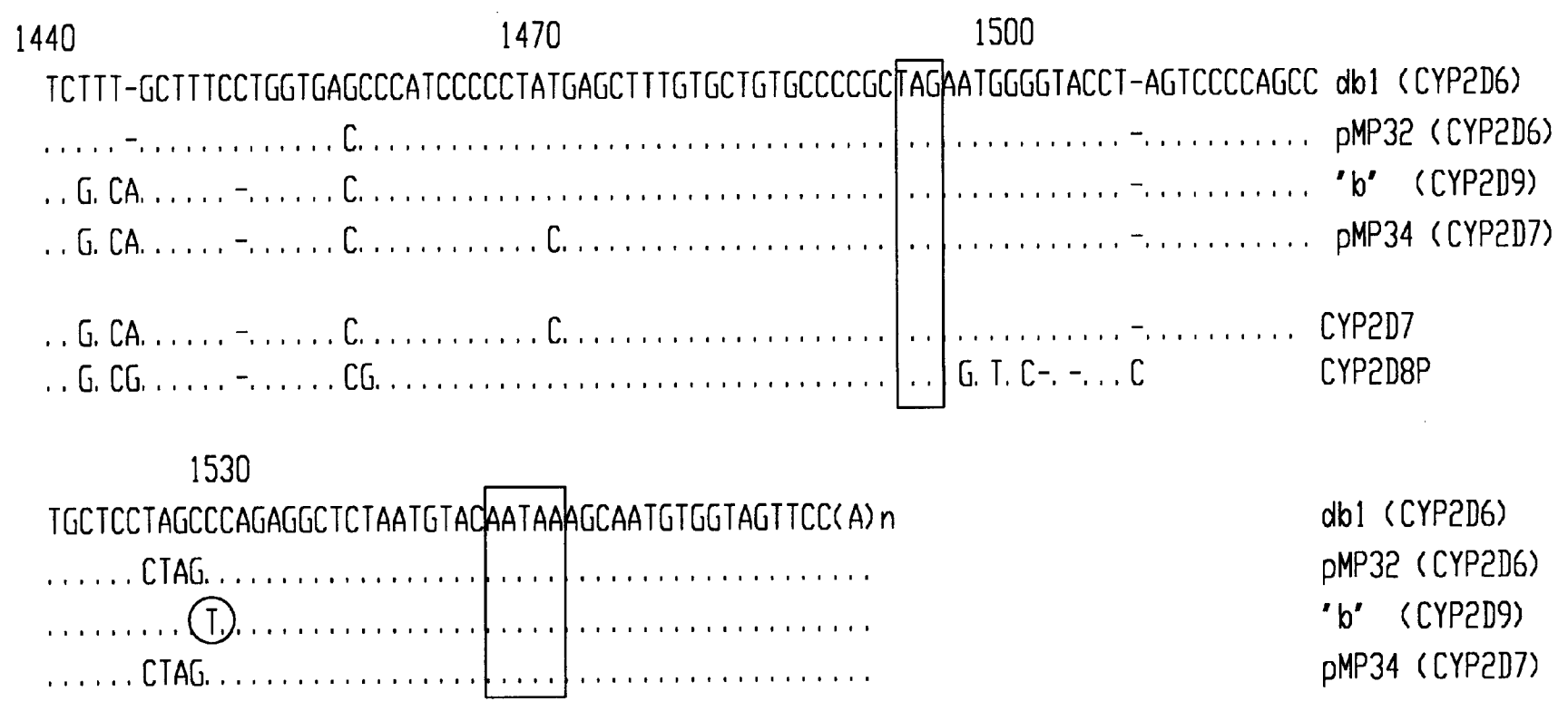

Referring to FIG. 7, an assay based on amplification using the oligonucleotides marked 2 and 3 followed by digestion with HhaI may be used to show the presence or absence of the G to A transition at bp 1094. In this case all other IID sequences will cut apart from the "b" variant. This is informative for the PM phenotype. Thus, the region of DNA between 1049 and 1173 is amplified, exposed to HhaI and submitted to gel electrophoresis followed by labelling with suitable probes. For the "b" variant, two fragments of 45 and 79 bases will be produced, whereas for EM phenotypes a single fragment of 124 bases is produced. This is an example of an indirect assay for the bp deletion at 506 in the CYPD2D6 gene.

EXAMPLE 6

Figure 9:
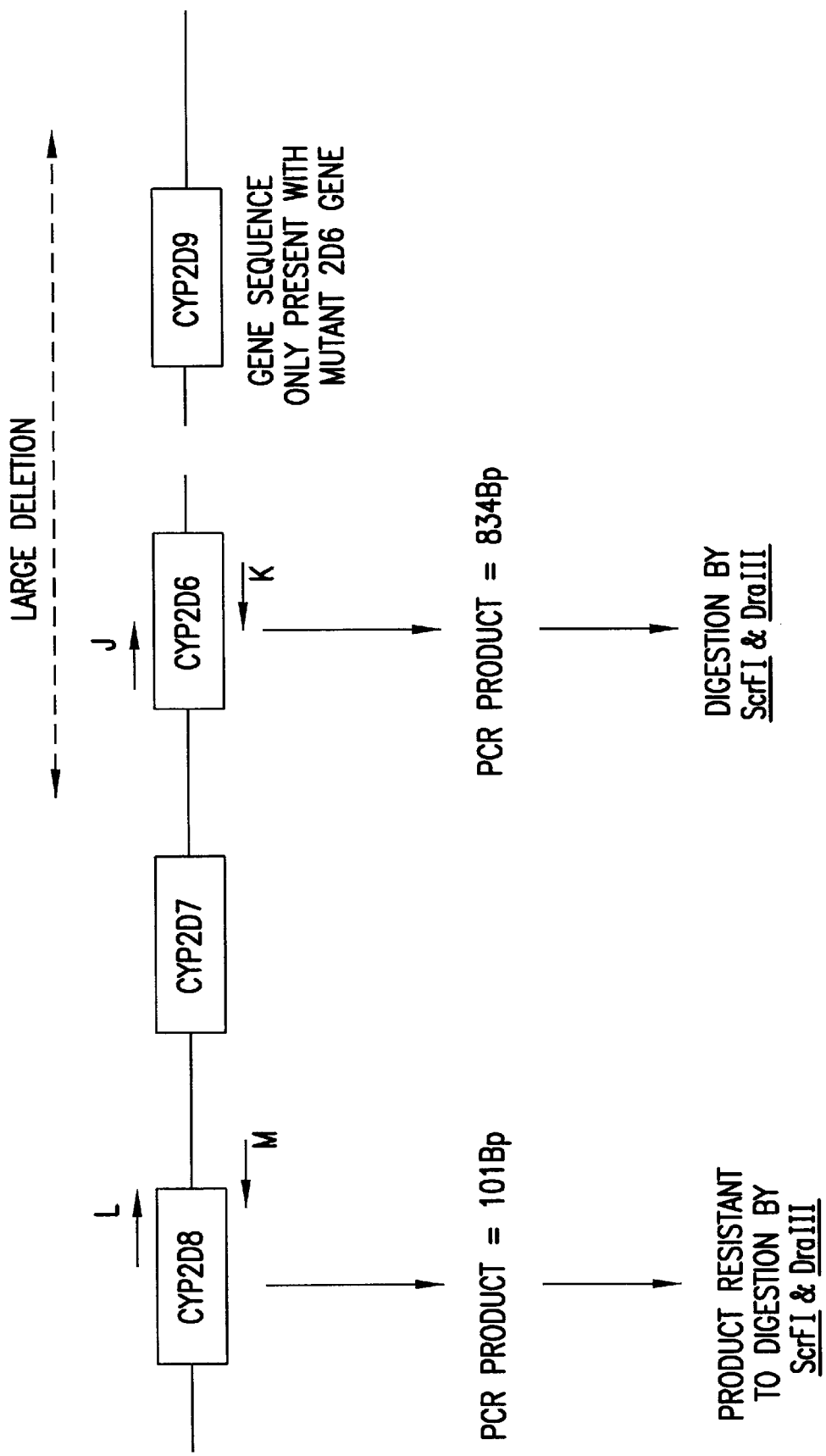
FIG. 9: This illustrates schematically the simultaneous use of primers J, K, L and M followed by digestion with ScrFI/DraIII for detection of the deletion of CYP2D6, single base deletion at position 2637 in exon 5 of CYP2D6 and G→A transition at 506, with amplification of CYP2D8 as a control.
Figure 10A:
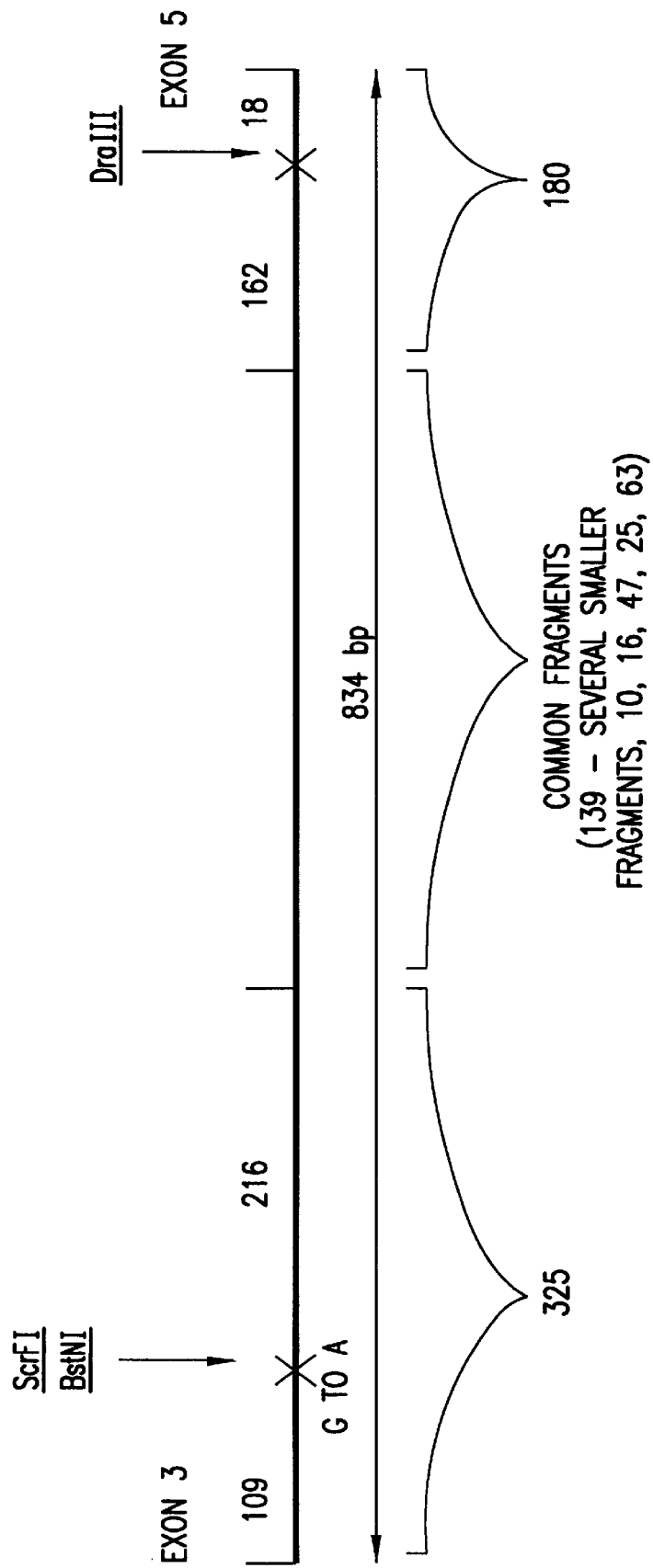
Figure 10B:
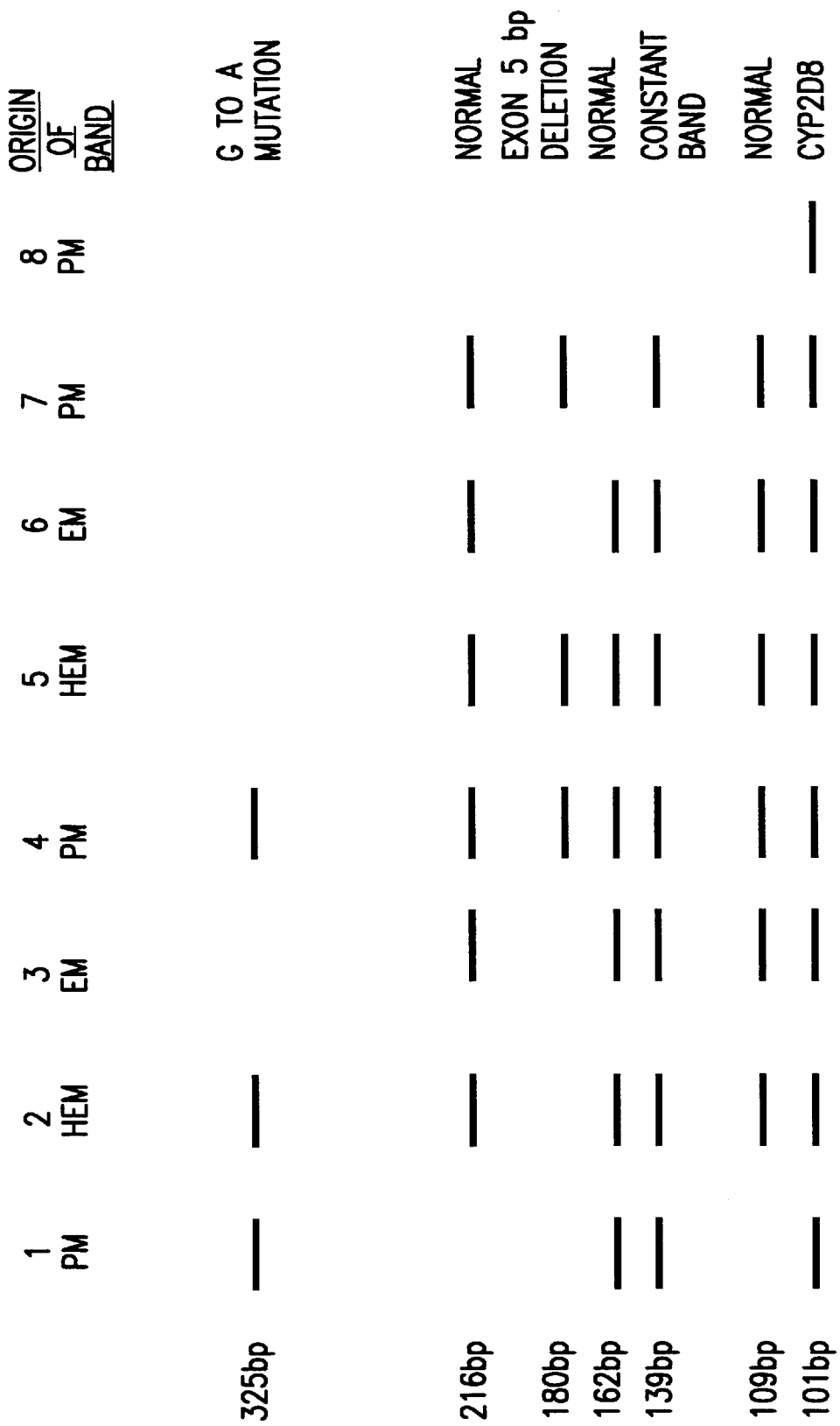
FIG. 10(b) is a schematic representation of all feasible patterns obtained by ScrFI/DraIII digestion of amplification products. The band sizes and separations correspond to those seen on nondenaturing polyacrylamide gel electrophoresis (PAGE). PM=poor metabolizer, HEM=heterozygote, EM=homozygous extensive metabolizer. The mutations in the PM's are as follows: Track 1: Homozygous for the G to A transition (mutation 1) or heterozygous for mutation 1 and the gene deletion. Track 4: Heterozygous for the bp deletion in exon 5 (mutation 2) and mutation 1. Track 7: Homozygous for mutation 2 or heterozygous for mutation 2 and the gene deletion. Track 8: Homozygous for the gene deletion (mutation 3).

In order to detect the gene deletion of CYP2D6 and the base deletion of 2637 in exon 5 of CYP2D6, primer J (5'-TGCCGCCTTCGCCAACCACT-3' (SEQ ID NO:9), bp 1824–1843) hybridising to exon 3 of CYP2D6 of the gene sequence and primer K (5'-GGCTGGGTCCGAGGTCACCC-3' (SEQ ID NO:10), bp 2657–2638) hybridising to exon 5 (FIG. 9) are used. The bold letters show the mismatched base pairs in primer K. The substitution of a C for an A introduces a DraIII restriction site (CCCGTG) into the pcr product in exon 5 in the normal allele. As a consequence of the base deletion, in PM's with this mutation the pcr product has the sequence CCCGTG which is resistant to digestion by DraIII. The G mismatch in the oligonucleotide is used to delete an ScrFI site which would otherwise complicate the assay. The G to A transition is analysed with the enzyme ScrFI. In addition to these pcr primers two more from the pseudogene CYP2D8 L (5'-CGGCCCAGCCACTCTCGTGT-3'(SEQ ID NO:11), bp 5141–5160) and M (5'-AACAGGGTCCCAGCTGAGGAG-3' (SEQ ID NO:12), bp 5241–5221) are preferably included in the reaction mixture (FIG. 9). This produces a constant band in all individuals and ensures that the amplification has occurred. This therefore also allows the identification of individuals who are homozygous for the gene deletion where no PCR product using the CYP2D6 PCR primers is obtained. The analysis conditions for the assay are given below and the interpretation of the banding patterns is shown in FIG. 10.

Analysis Conditions

1. PCR Amplification Reaction Components
   50 to 500 ng DNA*
   40 nmol $MgCl_2$
   300 ng of each primer J and K
   150 ng of each primer L and M
   200 nmol DATP, dCTP, DGTP and dTTP
   1.5 U TUB polymerase (Amersham Corp.)
   (All other conditions as per manufacturers' recommendations).

2. PCR Conditions
   Following initial denaturation at 95° C. for 3 min, 30 cycles of PCR are carried out at 94° C. for 1 min, 60° C. for 1 min and 72° for 1 minute. A final step of 72° C. for 2 minutes is added at the end.

3. 75% of the final reaction is removed. The remaining 25% is digested for 2 hr with 3 units of both ScrFI and DraIII at 37° C. under oil.

4. The whole (30 μl) reaction mixture is then subject to gel electrophoresis on 8% polyacrylamide gels for 1 to 2 hrs.

5. DNA banding pattern is then visualised by u/v excitation for ethidium bromide staining.

* As an alternative to DNA, whole blood can be taken for the assay. This is treated as follows. For 100 μl whole blood, wash and spin down cells 3 times with 10 mM Tris/HCI pH 8.0 containing 1 mM EDTA. Then treat with lysis buffer: KCl (50 mM), Tris/HCl, pH 8.3 (20 mM); $MgCl_2$ (2.5 mM); 0.45% v/v Tween 20; 0.45% v/v Nonident P40 and proteinase K (200 μg/ml). Vortex and incubate at 55° C. for 20 min. Then add 100 μl of $H_2O$ and heat to 90° C. for 10 min. Take 10 μl of this solution for the PCR reaction.

This analysis method is very rapid, taking approximately 6 hrs. It also has the advantage that it requires only very small amounts of starting materials. We currently carry out the analysis on approximately 10 μl of whole blood. This together with the use of high speed cycling methods should enable this protocol to be shortened to under 2 hours. This would allow a single individual to process up to 500 samples per day.

REFERENCES

The following documents are specifically incorporated herein by reference.

1. Eichelbaum, M (1988) *Atlas of Science: Pharmacology*, pp. 243–251.
2. Gonzalez, F. J., Skoda, R. C., Kimura, S., Umeno, M., Zanger, U. M., Nebert, D. W., Gelboin, H. V., Hardwick, J. P. & Meyer, U. A. (1988) *Nature,* 331, 442–446.
3. Nebert, D. W., Nelson, D. R., Adesnik, M., Coon, M. J., Estabrook, R. W., Gonzalez, F. J., Guengerich, F. P., Gunsalus, I. C., Johnson, E. F., Kemper, B., Levin, W., Phillips, I. R., Sato, R. & Waterman, M. R. (1989) *DNA* 8, 1–14.
4. Skoda, R. C., Gonzalez, F. J., Demierre, A., & Meyer, U. A. (1988) *Proc. Natl. Acad. Sci. U.S.A.* 85, 5240–5243.
5. Saiki, R. K., et al (1988), *Science* 239, 487–91.
6. Feinberg, D. P. & Vogelstein, B. (1983) *Anal. Biochem.* 136, 6–13.
7. Kwok, S. C. M., Ledley, F. D., DiLella, A. G., Robson, K. J. H., & Woo, S. L. C. (1985) *Biochem* 24, 556–561.
8. Sanger, F., Coulson, A. R., Barrell, B. G., Smith, A. J. H., & Roe, B. A. (1980) *J. Mol. Biol.* 143, 161–178.
9. Biggin, M. D., Gibson, T. J., & Hong, G. F. (1983) *Proc. Natl. Acad. Sci. U.S.A.* 80 , 3963–3965.
10. Staden, R. (1986) *Nucl. Acids. Res.* 14, 217–231.
11. Kimura, S., Urmeno, M., Skoda, R. C., Meyer, U. A. and Gonzalez, F. J. (1989) *Am. J. Hu. Genet.* 45, 889–904

We claim:

1. A method of determining the EM/PM phenotype of an individual or a cell derived from an individual comprising the steps of:

(1) removing material containing DNA from an individual or a cell derived from an individual and extracting said DNA if desired, (2) analyzing said DNA for a mutation at one or more of positions 100, 271, 281, 294, 408, 506 or 1432 of the DNA sequence of P450 IID bufuralol-1'-hydroxylase using a reagent capable of distinguishing one nucleotide from another or the presence or absence of a nucleotide at a given site in the DNA and (3) deducing the EM/PM phenotype by comparing the results of step (2) with the results obtained from individuals with known PM and EM phenotypes.

2. The method according to claim 1 wherein said reagent is a restriction enzyme which will cut, or will not cut, at or adjacent to one of the said positions according to whether the mutation is present.

3. The method according to claim 1 wherein sample DNA is subjected to the polymerase chain reaction using oligonucleotide primers which are capable of hybridising selectively either to the wild-type or to the mutant sequence at the location being analysed, such that the generation of amplified DNA will indicate whether said mutation is present.

4. A method of determining the EM/PM phenotype of an individual or a cell derived from an individual comprising the steps of:

(1) removing material containing DNA from an individual or a cell derived from an individual and extracting the said DNA it desired, (2) analyzing said DNA for a mutation at one or more of positions 271, 281, 294 or 506 of the DNA sequence of P450 IID bufuralol-1'-hydroxylase using a reagent capable of distinguishing one nucleotide from another or the presence or absence of a nucleotide at a given site in the DNA and (3) deducing the EM/PM phenotype by comparing the results of step (2) with the results obtained from individuals with known PM and EM phenotypes.

5. The method according to claim 4 wherein a base-pair deletion at position 506 is detected.

6. The method according to claim 2 further comprising before step (2) the step of amplifying the amount of a selected region of said DNA.

7. The method according to claim 2 or 6, wherein a base-pair deletion at position 506 is detected, said restriction enzyme is BstNI or an isoschizomer thereof and said DNA is obtained from a cell of a human individual.

8. A method of identifying a mutation in the DNA sequence of P450IID bufuralol-1'-hydroxylase at one or more of positions 100, 271, 281, 294, 408, 506, 775 or 1432 comprising (1) subjecting the sample DNA to the polymerase chain reaction using oligonucleotide primers which are capable of hybridising selectively either to the wild-type or to the mutant sequence at the location being analysed, the primers being such as to introduce, upon hybridisation to the said location, a restriction site which is not present in the wild-type or mutated location and (2) subjecting amplified DNA derived from step (1) to a restriction digest with an enzyme which cleaves at said restriction site.

9. The method according to claim 8 wherein two pairs of primers are used in step (1), one pair hybridising on respective sides of position 506 and the other pair hybridising on respective sides at position 775.

10. A single-stranded DNA compound suitable for use as a primer in a polymerase chain reaction, the compound being capable of hybridising to a region of wild-type or mutant bufuralol-1'-hydroxylase-encoding DNA flanking positions 100, 271, 281, 294, 408, 506 or 1432 such that, in the polymerase chain reaction, DNA synthesis will or will not proceed from the primer towards said position according to whether there is a mutation at the said position.

11. A compound selected from the group consisting of:

(A) 5'-TTGCGGCGCCGCTTCGGGGA-3' (SEQ ID NO:1)

(B) 5-CTTGGGAACGCGGCCCGAAA-3' (SEQ ID NO:2)

(C) 5'-CGCCTTCGCCAACCACTCCG-3' (SEQ ID NO:3)

(D) 5'-AAATCCTGCTCTTCCGAGGC-3' (SEQ ID NO:4)

(E) 5'-GCCGCCGTGCATGCCTCG-3' (SEQ ID NO:7)

(F) 5'-GGAACTACCACATTGCTTT-3' (SEQ ID NO:8)

(G) 5'-GATGAGCTGCTAACTGAGCCC-3' (SEQ ID NO:5)

(H) 5'-CCGAGAGCATACTCGGGAC-3' (SEQ ID NO:6)

(J) 5'-TGCCGCCTTCGCCAACCACT-3' (SEQ ID NO:9)

(K) 5'-GGCTGGGTCCGAGGTCACCC-3' (SEQ ID NO:10)

(L) 5'-CGGCCCAGCCACTCTCGTGT-3' (SEQ ID NO:11)

(M) 5'-AACAGGGTCCCAGCTGAGGAG-3' (SEQ ID NO:12).

12. A kit for performing the method of claim 1 comprising a compound according to claim 10 or 11.

13. A kit according to claim 12 further comprising at least one restriction enzyme for distinguishing a polymorphism characteristic of the EM or PM phenotype.

```
                        SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

TTGCGGCGCC GCTTCGGGGA                                                    20

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CTTGGGAACG CGGCCCGAAA                                                    20

(2) INFORMATION FOR SEQ ID NO:3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO
```

(xi) SEQUENCE DESCRIPTION: SEQ ID NO:3:

CGCCTTCGCC AACCACTCCG                                                      20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

AAATCCTGCT CTTCCGAGGC                                                      20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GATGAGCTGC TAACTGAGCC C                                                    21

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

CCGAGAGCAT ACTCGGGAC                                                       19

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

GCCGCCGTGC ATGCCTCG                          18

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

GGAACTACCA CATTGCTTT                         19

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

TGCCGCCTTC GCCAACCACT                        20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

GGCTGGGTCC GAGGTCACCC                        20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

CGGCCCAGCC ACTCTCGTGT                                                    20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

AACAGGGTCC CAGCTGAGGA G                                                  21

(2) INFORMATION FOR SEQ ID NO:13:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:13:

```
ATGGGGCTAG AAGCACTGGT GCCCCTGGCC GTGATAGTGG CCATCTTCCT GCTCCTGGTG      60
GACCTGATGC ACCGGCGCCA ACGCTGGGCT GCACGCTACC CACCAGGCCC CCTGCCACTG     120
CCCGGGCTGG GCAACCTGCT GCATGTGGAC TTCCAGAACA CACCATACTG CTTCGACCAG     180
TTGCGGCGCC GCTTCGGGGA CGTGTTCAGC CTGCAGCTGG CCTGGACGCC GGTGGTCGTG     240
CTCAATGGGC TGGCGGCCGT GCGCGAGGCG CTGGTGACCC ACGGCGAGGA CACCGCCGAC     300
CGCCCGCCTG TGCCCATCAC CCAGATCCTG GGTTTCGGGC GCGTTCCCA AGGGGTGTTC      360
CTGGCGCGCT ATGGGCCCGC GTGGCGCGAG CAGAGGCGCT TCTCCGTGTC CACCTTGCGC     420
AACTTGGGCC TGGGCAAGAA GTCGCTGGAG CAGTGGGTGA CCGAGGAGGC CGCCTGCCTT     480
TGTGCCGCCT TCGCCAACCA CTCCGGACGC CCCTTTCGCC CCAACGGTCT CTTGGACAAA     540
GCCGTGAGCA ACGTGATCGC CTCCCTCACC TGCGGGCGCC GCTTCGAGTA CGACGACCCT     600
CGCTTCCTCA GGCTGCTGGA CCTAGCTCAG GAGGGACTGA AGGAGGAGTC GGGCTTTCTG     660
CGCGAGGTGC TGAATGCTGT CCCCGTCCTC CTGCATATCC CAGCGCTGGC TGGCAAGGTC     720
CTACGCTTCC AAAAGGCTTT CCTGACCCAG CTGGATGAGC TGCTAACTGA GCACAGGATG     780
ACCTGGGACC CAGCCCAGCC CCCCCGAGAC CTGACTGAGG CCTTCCTGGC AGAGATGGAG     840
AAGGCCAAGG GGAACCCTGA GAGCAGCTTC AATGATGAGA ACCTGCGCAT AGTGGTGGCT     900
GACCTGTTCT CTGCCGGGAT GGTGACCACC TCGACCACGC TGGCCTGGGG CCTCCTGCTC     960
ATGATCCTAC ATCCGGATGT GCAGCCGTGT CCAACAGGAG ATCGACGACG TGATAGGGCA    1020
GGTGCGGCGA CCAGAGATGG GTGACCAGGC TCACATGCCC TACACCACTG CCGTGATTCA    1080
```

-continued

```
TGAGGTGCAG CGCTTTGGGG ACATCGTCCC CCTGGGTATG ACCCATATGA CATCCCGTGA    1140

CATCGAAGTA CAGGGCTTCC GCATCCCTAA GGGAACGACA CTCATCACCA ACCTGTCATC    1200

GGTGCTGAAG GATGAGGCCG TCTGGGAGAA GCCCTTCCGC TTCCACCCCG AACACTTCCT    1260

GGATGCCCAG GGCCACTTTG TGAAGCCGGA GGCCTTCCTG CCTTTCTCAG CAGGCCGCCG    1320

TGCATGCCTC GGGGAGCCCC TGGCCCGCAT GGAGCTCTTC CTCTTCTTCA CCTCCCTGCT    1380

GCAGCACTTC AGCTTCTCGG TGCCCACTGG ACAGCCCCGG CCCAGCCACC ATGGTGTCTT    1440

TGCTTTCCTG GTGAGCCCAT CCCCCTATGA GCTTTGTGCT GTGCCCCGCT AGAATGGGGT    1500

ACCTAGTCCC CAGCCTGCTC CTAGCCCAGA GGCTCTAATG TACAATAAAG CAATGTGGTA    1560

GTTCCA                                                               1566
```

(2) INFORMATION FOR SEQ ID NO:14:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:14:

```
TGGGGACGCA TGTCTGTCCA GTCCGTGTCC AACAGGAGAT CGACGACGTG ATAGGGCAGG      60

TGCGGCGACC AGAGATGGGT GACCAGGCTC ACATGCCCTA CACCACTGCC GTGATTCACG     120

AGGTGCAGCG CTTTGGGGAC ATCATCCCCC TGAGTGTGAC CCATATGACA TCCCATGACA     180

TCGAAGTACA GGGCTTCCGC ATCCCTAAGG GAACGACACT CATCACCAAC CTGT           234
```

(2) INFORMATION FOR SEQ ID NO:15:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:15:

```
TGGGGACGCA TGTCTGTCCA TGCCGTGTCC AACAGATCGA CAACGTGATA GGGCAGGTGT      60

GGTGACCAGA GATGGGTGAC CAGGCTCGCA TGCCCTGCAC CACTGCCGTG ATTCACGAGG     120

TGCAGCGCTT TGGGGACATC GTCCCCCTGG GTGTGACCCA TATGCATCC CGTGACATCG      180

AAGTACAGGG CTTCCGCATC CCTAAGGGAT GATGCTCTTC ACCAACCTGT                230
```

(2) INFORMATION FOR SEQ ID NO:16:

(i) SEQUENCE CHARACTERISTICS:
        (A) LENGTH: 235 base pairs
        (B) TYPE: nucleic acid (C) STRANDEDNESS: single
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:16:

```
TGGGGACGCA TGTCTGTCCA GGCCCGTGTC CAACAGGAGA TCGACGACGT GATAGGGCAG      60

GTGCGGCGAC CAGAGATGGG TGACCAGGCT CACATGCCCT ACACCACTGC CGTGATTCAT     120

GAGGTGCAGC GCTTTGGGGA CATCGTCCCC CTGGGTATGA CCCATATGAC ATCCCGTGAC     180

ATCGAAGTAC AGGGCTTCCG CATCCCTAAG GGAACGACAC TCATCACCAA CCTGT          235
```

(2) INFORMATION FOR SEQ ID NO:17:

(i) SEQUENCE CHARACTERISTICS:
            (A) LENGTH: 234 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:17:

```
TGGGGACGCA TGTCTGTCCA GTCCGTGTCC AACAGGAGAT CGACGACGTG ATAGGGCAGG      60

TGCGGCGACC AGAGATGGGT GACCAGGCTC ACATGCCCTA CACCACTGCC GTGATTCACG     120

AGGTGCAGCG CTTTGGGGAC ATCATCCCCC TGAGTGTGAC CCATATGACA TCCCGTGACA     180

TCGAAGTACA GGGCTTCCGC ATCCCTAAGG GAACGACACT CATCACCAAC CTGT           234
```

(2) INFORMATION FOR SEQ ID NO:18:

(i) SEQUENCE CHARACTERISTICS:
            (A) LENGTH: 237 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:18:

```
TGGGGACGCA TGTCTGTCCA GTTGCCCGTG TCCAACAGGA GATCGACGAC GTGATAGGGC      60

AGGTGCGGCG ACCAGAGATG GGTGACCAGG CTCACATGCC CTACACCACT GCCGTGATTC     120

ATGAGGTGCA GCACTTTGGG GACATCGTCC CCTGGGTGT GACCCATATG ACATCCCGTG      180

ACATCGAAGT ACAGGGCTTC CGCATCCCTA AGGGAACGAC ACTCATCACC AACCTGT        237
```

(2) INFORMATION FOR SEQ ID NO:19:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:19:

```
TGGGGACGCA TGTCTGTCCA GGCCCGTGTC CAACAGGAGA TCGACGACGT GATAGGGCAG      60

GTGCGGCGAC CAGAGATGGG TGACCAGGCT CACATGCCCT ACACCACTGC CGTGATTCAT     120

GAGGTGCAGC GCTTTGGGGA CATCGTCCCC CTGGGTGTGA CCCATATGAC ATCCCGTGAC     180

ATCGAAGTAC AGGGCTTCCG CATCCCTAAG GGAACGACAC TCATCACCAA CCTGT         235
```

(2) INFORMATION FOR SEQ ID NO:20:

(i) SEQUENCE CHARACTERISTICS:
        (A) LENGTH: 1568 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:20:

```
ATGGGGCTAG AAGCACTGGT GCCCCTGGCC GTGATAGTGG CCATCTTCCT GCTCCTGGTG      60

GACCTGATGC ACCGGCGCCA ACGCTGGGCT GCACGCTACT CACCAGGCCC CCTGCCACTG     120

CCCGGGCTGG GCAACCTGCT GCATGTGGAC TTCCAGAACA CACCATACTG CTTCGACCAG     180

TGTTCGCGCC GCTTCGGGGA CGTGTTCAGC CTGCAGCTGG CCTGGACGCC GGTGGTCGTG     240

CTCAATGGGC TGGCGGCCGT GCGCGAGGCG ATGGTGACCC GCGGCGAGGA CACGGCCGAC     300

CGCCCGCCTG TGCCCATCAC CCAGATCCTG GGTTTCGGGC GCGTTCCCA AGGGGTGTTC      360

CTGGCGCGCT ATGGGCCCGC GTGGCGCGAG CAGAGGCGCT TCTCCGTCTC CACCTTGCGC     420

AACTTGGGCC TGGGCAAGAA GTCGCTGGAG CAGTGGGTGA CCGAGGAGGC CGCCTGCCTT     480

TGTGCCGCCT TCGCCAACCA CTCCGACGCC CCTTTCGCCC CAACGGTCTC TTGGACAAAG     540

CCGTGAGCAA CGTGATCGCC TCCCTCACCT GCGGGCGCCG CTTCGAGTAC GACGACCCTC     600

GCTTCCTCAG GCTGCTGGAC CTAGCTCAGG AGGGACTGAA GGAGGAGTCG GGCTTTCTGC     660

GCGAGGTGCT GAATGCTGTC CCCGTCCTCC TGCATATCCC AGCGCTGGCT GGCAAGGTCC     720

TACGCTTCCA AAAGGCTTTC CTGACCCAGC TGGATGAGCT GCTAACTGAG CACAGGATGA     780

CCTGGGACCC AGCCCAGCCC CCCCGAGACC TGACTGAGGC CTTCCTGGCA GAGATGGAGA     840

AGGCCAAGGG GAACCCTGAG AGCAGCTTCA ATGATGAGAA CCTGCGCATA GTGGTGGCTG     900

ACCTGTTCTC TGCCGGGATG GTGACCACCT CGACCACGCT GGCCTGGGGC CTCCTGCTCA     960
```

-continued

```
TGATCCTACA TCCGGATGTG CAGCGCCCGT GTCCAACAGG AGATCGACGA CGTGATAGGG    1020

CAGGTGCGGC GACCAGAGAT GGGTGACCAG GCTCACATGC CCTACACCAC TGCCGTGATT    1080

CATGAGGTGC AGCGCTTTGG GGACATCGTC CCCCTGGGTG TGACCCATAT GACATCCCGT    1140

GACATCGAAG TACAGGGCTT CCGCATCCCT AAGGGAACGA CACTCATCAC CAACCTGTCA    1200

TCGGTGCTGA AGGATGAGGC CGTCTGGGAG AAGCCCTTCC GCTTCCACCC CGAACACTTC    1260

CTGGATGCCC AGGGCCACTT TGTGAAGCCG GAGGCCTTCC TGCCTTTCTC AGCAGGCCGC    1320

CGTGCATGCC TCGGGGAGCC CCTGGCCCGC ATGGAGCTCT TCCTCTTCTT CACCTCCCTG    1380

CTGCAGCACT TCAGCTTCTC GGTGCCCACT GGACAGCCCC GGCCCAGCCA CCATGGTGTC    1440

TTTGCTTTCC TGGTGACCCC ATCCCCCTAT GAGCTTTGTG CTGTGCCCCG CTAGAATGGG    1500

GTACCTAGTC CCCAGCCTGC TCCCTAGCCA GAGGCTCTAA TGTACAATAA AGCAATGTGG    1560

TAGTTCCA                                                             1568
```

(2) INFORMATION FOR SEQ ID NO:21:

(i) SEQUENCE CHARACTERISTICS:
        (A) LENGTH: 1571 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:21:

```
ATGGGGCTAG AAGCACTGGT GCCCCTGGCC GTGATAGTGG CCATCTTCCT GCTCCTGGTG      60

GACCTGATGC ACCGGCGCCA ACGCTGGGCT GCACGCTACC CACCAGGCCC CCTGCCACTG     120

CCCGGGCTGG GCAACCTGCT GCATGTGGAC TTCCAGAACA CACCATACTG CTTCGACCAG     180

TTGCGGCGCC GCTTCGGGGA CGTGTTCAGC CTGCAGCTGG CCTGGACGCC GGTGGTCGTG     240

CTCAATGGGC TGGCGGCCGT GCGCGAGGCG CTGGTGACCC ACGGCGAGGA CACCGCCGAC     300

CGCCCGCCTG TGCCCATCAC CCAGATCCTG GGTTTCGGGC GCGTTCCCA AGGGGTGTTC      360

CTGGCGCGCT ATGGGCCCGC GTGGCGCGAG CAGAGGCGCT TCTCCGTGTC CACCTTGCGC     420

AACTTGGGCC TGGGCAAGAA GTCGCTGGAG CAGTGGGTGA CCGAGGAGGC CGCCTGCCTT     480

TGTGCCGCCT TCGCCGACCA AGCCGGACGC CCCTTTCGCC CCAACGGTCT CTTGGACAAA     540

GCCGTGAGCA ACGTGATCGC CTCCCTCACC TGCGGGCGCC GCTTCGAGTA CGACGACCCT     600

CGCTTCCTCA GGCTGCTGGA CCTAGCTCAG GGAGGGATCG AAGGAGGAGT CGGGCTTCCT     660

GCGCGAGGTG CTGAATGCTG TCCCCGTCCT CCCGCACATC CCAGCGCTGG CTGGCAAGGT     720

CCTACGCTTC CAAAAGGCTT TCCTGACCCA GCTGGATGAG CTGCTAACTG AGCACAGGAT     780

GACCTGGGAC CCAGCCCAGC CACCCCGAGA CCTGACTGAG GCCTTCCTGG CAAAGAAGGA     840

GAAGGCCAAG GGGAGCCCTG AGAGCAGCTT CAATGATGAG AACCTGCGCA TAGTGGTGGG     900

TAACCTGTTC CTTGCCGGGA TGGTGACCAC CTTGACCACG CTGGCCTGGG GCTCCTGCT     960

CATGATCCTA CACCTGGATG TGCATGCGCC CGTGTCCAAC AGGAGATCGA CGACGTGATA    1020

GGGCAGGTGC GGCGACCAGA GATGGGTGAC CAGGCTCACA TGCCCTACAC CACTGCCGTG    1080

ATTCATGAGG TGCAGCACTT TGGGGACATC GTCCCCCTGG GTGTGACCCA TATGACATCC    1140
```

```
CGTGACATCG AAGTACAGGG CTTCCGCATC CCTAAGGGAA CGACACTCAT CACCAACCTG   1200

TCATCGGTGC TGAAGGATGA GGCCGTCTGG GAGAAGCCCT TCCGCTTCCA CCCCGAACAC   1260

TTCCTGGATG CCCAGGGCCA CTTTGTGAAG CCGGAGGCCT TCCTGCCTTT CTCAGCAGGC   1320

CGCCGTGCAT GCCTCGGGGA GCCCCTGGCC CGCATGGAGC TCTTCCTCTT CTTCACCTCC   1380

CTGCTGCAGC ACTTCAGCTT CTCCGTGGCC GCCGGACAGC CCCGGCCCAG CCACTCTCGT   1440

GTCGTCAGCT TTCTGGTGAC CCCATCCCCC TATGAGCTTT GTGCTGTGCC CCGCTAGAAT   1500

GGGGTACCTA GTCCCCAGCC TGCTCCTAGC TCAGAGGCTC TAATGTACAA TAAAGCAATG   1560

TGGTAGTTCC A                                                        1571
```

(2) INFORMATION FOR SEQ ID NO:22:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:22:

```
ATGGGGCTAG AAGCACTGGT GCCCCTGGCC GTGATAGTGG CCATCTTCCT GCTCCTGGTG     60

GACCTGATGC ACCGGCGCCA ACGCTGGGCT GCACGCTACC CACCAGGCCC CCTGCCACTG    120

CCCGGGCTGG GCAACCTGCT GCATGTGGAC TTCCAGAACA CACCATACTG CTTCGACCAG    180

TTGCGGCGCC GCTTCGGGGA CGTGTTCAGC CTGCAGCTGG CCTGGACGCC GGTGGTCGTG    240

CTCAATGGGC TGGCGGCCGT GCGCGAGGCG CTGGTGACCC ACGGCGAGGA CACCGCCGAC    300

CGCCCGCCTG TGCCCATCAC CCAGATCCTG GGTTTCGGGC GCGTTCCCA AGGGGTGTTC    360

CTGGCGCGCT ATGGGCCCGC GTGGCGCGAG CAGAGGCGCT TCTCCGTGTC CACCTTGCGC    420

AACTTGGGCC TGGGCAAGAA GTCGCTGGAG CAGTGGGTGA CCGAGGAGGC CGCCTGCCTT    480

TGTGCCGCCT TCGCCAACCA CTCCGGACGC CCCTTTCGCC CAACGGTCT CTTGGACAAA    540

GCCGTGAGCA ACGTGATCGC CTCCCTCACC TGCGGGCGCC GCTTCGAGTA CGACGACCCT    600

CGCTTCCTCA GGCTGCTGGA CCTAGCTCAG GAGGGACTGA AGGAGGAGTC GGGCTTTCTG    660

CGCGAGGTGC TGAATGCTGT CCCCGTCCTC CTGCATATCC CAGCGCTGGC TGGCAAGGTC    720

CTACGCTTCC AAAAGGCTTT CCTGACCCAG CTGGATGAGC TGCTAACTGA GCACAGGATG    780

ACCTGGGACC CAGCCCAGCC CCCCCGAGAC CTGACTGAGG CCTTCCTGGC AGAGATGGAG    840

AAGGCCAAGG GGAACCCTGA GAGCAGCTTC AATGATGAGA ACCTGCGCAT AGTGGTGGCT    900

GACCTGTTCT CTGCCGGGAT GGTGACCACC TCGACCACGC TGGCCTGGGG CCTCCTGCTC    960

ATGATCCTAC ATCCGGATGT GCATCCGTGT CCAACAGGAG ATCGACGACG TGATAGGGCA   1020

GGTGCGGCGA CCAGAGATGG GTGACCAGGC TCACATGCCC TACACCACTG CCGTGATTCA   1080

CGAGGTGCAG CGCTTTGGGG ACATCATCCC CCTGAGTGTG ACCCATATGA CATCCCGTGA   1140

CATCGAAGTA CAGGGCTTCC GCATCCCTAA GGGAACGACA CTCATCACCA ACCTGTCATC   1200

GGTGCTGAAG GATGAGGCCG TCTGGAAGAA GCCCTTCCGC TTCCACCCCG AACACTTCCT   1260

GGATGCCCAG GGCCACTTTG TGAAGCCGGA GGCCTTCCTG CCTTTCTCAG CAGGCCGCCG   1320
```

```
TGCATGCCTC GGGGAGCCCC TGGCCCGCAT GGAGCTCTTC CTCTTCTTCA CCTCCCTGCT    1380

GCAGCACTTC AGCTTCTCCG TGGCCGCCGG ACAGCCCCGG CCCAGCCACT CTCGTGTCGT    1440

CAGCTTTCTG GTGACCCCAT CCCCCTACGA GCTTTGTGCT GTGCCCCGCT AGAATGGGGT    1500

ACCTAGTCCC CAGCCTGCTC CCTAGCCAGA GGCTCTAATG TACAATAAAG CAATGTGGTA    1560

GTTCCA                                                              1566
```

(2) INFORMATION FOR SEQ ID NO:23:

(i) SEQUENCE CHARACTERISTICS:
        (A) LENGTH: 1569 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:23:

```
ATGGGGCTAG AAGCACTGGT GCCCCTGGCC ATGATAGTGG CCATCTTCCT GCTCCTGGTG      60

GACCTGATGC ACCGGCACCA ACGCTGGGCT GCACGCTACC CGCCAGGTCC CCTGCCACTG     120

CCCGGGCTGG GCAACCTTGC TGCATGTGGA CTTCCAGAAC ACACCATACT GCTTCGACCA     180

GTTGCGGCGC CGCTTCGGGG ACGTGTTCAG CCTGCAGCTG GCCTGGACGC CGGTGGTCGT     240

GCTCAATGGG CTGGCGGCCG TGCGCGAGGC GATGGTGACC CGCGGCGAGG ACACGGCCGA     300

CCGCCCGCCT GCGCCCATCT ACCAGGTCCT GGGCTTCGGG CCGCGTTCCC AAGGGGTGTT     360

CCTGGCGCGC TATGGGCCCG CGTGGCGCGA GCAGAGGCGC TTCTCCGTGT CCACCTTGCG     420

CAACTTGGGC CTGGGCAAGA AGTCGCTGGA GCAGTGGGTG ACCGAGGAGG CCGCCTGCCT     480

TTGTGCCGCC TTCGCCGACC AAGCCGGACC GCCCTTTCGC CCCAACGGTC TCTTGGACAA     540

AGCCGTGAGC AACGTGATCG CCTCCCTCAC CTGCGGGCGC CGCTTCGAGT ACGACGACCC     600

TCGCTTCCTC AGGCTGCTGG ACCTAGCTCA GGAGGGACTG AAGGAGGAGT CGGGCTTCCT     660

GCGCGAGGTG CTGAATGCTG TCCCCGTCCT CCTGCACATC CCAGCGCTGG CTGGCAAGGT     720

CCTACGCTTC CAAAAGGCTT TCCTGACCCA GCTGGATGAG CTGCTAACTG AGCACAGGAT     780

GACCTGGGAC CCAGCCCAGC CCCCCGAGA CCTGACTGAG GCCTTCCTGG CAGAGATGGA     840

GAAGGCCAAG GGGAGCCCTG AGAGCAGCTT CAATGATGAG AACCTGCGCA TAGTGGTGGG     900

TAACCTGTTC CTTGCCGGGA TGGTGACCAC CTTGACCACG CTGGCCTGGG GCCTCCTGCT     960

CATGATCCTA CACCTGGATG TGCAGCTCCG TGTCCAACAG GAGATCGACG ACGTGATAGG    1020

GCAGGTGCGG CGACCAGAGA TGGGTGACCA GGCTCACATG CCCTACACCA CTGCCGTGAT    1080

TCACGAGGTG CAGCGCTTTG GGGACATCAT CCCCCTGAGT GTGACCCATA TGACATCCCA    1140

TGACATCGAA GTACAGGGCT TCCGCATCCC TAAGGGAACG ACACTCATCA CCAACCTGTC    1200

ATCGGTGCTG AAGGATGAGG CCGTCTGGAA GAAGCCCTTC CGCTTCCACC CCGAACACTT    1260

CCTGGATGCC CAGGGCCACT TTGTGAAGCC GGAGGCCTTC TGCCTTTCT CAGCAGGCCG    1320

CCGTGCATGC CTCGGGGAGC CCCTGGCCCG CATGGAGCTC TTCCTCTTCT TCACCTCCCT    1380

GCTGCAGCAC TTCAGCTTCT CCGTGGCCGC CGGACAGCCC CGGCCCAGCC ACTCTCGTGT    1440

CGTCAGCTTT CTGGTGACCC CATCCCCCTA CGAGCTTTGT GCTGTGCCCC GCTAGAATGG    1500
```

```
GGTACCTAGT CCCCAGCCTG CTCCTAGCTC AGAGGCTCTA ATGTACAATA AAGCAATGTG    1560

GTAGTTCCA                                                            1569
```

(2) INFORMATION FOR SEQ ID NO:24:

(i) SEQUENCE CHARACTERISTICS:
        (A) LENGTH: 1501 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:24:

```
ATGGGGCTGG ATGCACTGGT GCCCCTGGCA GTGACAGTGG CCATCTTCCT GCTCCTGGTG      60

GACCTGATGC AGCAGCACCA ACGCTGGACT GCACGCTACC CGCCAGGCCC CCTGCCACTG     120

CCCGGGCTGG GCAACTTGCT GCATGTGGAC TTCCAGAACA TATACACCTT CAACCAGCTG     180

CGGCACCGCT TTGGGACGT GTTCAGCCTG CAGCTGGCCT GGATGCCGGT GGTCGTGCTC      240

AATGGGCTGG CGGCCGTGCG TGAGGCTCTG GTGACCTGCG GCGAGGACAC CGCCGACCGC     300

CCGCCTGCGC CCATCTACCA GGTCCTGGGC ATCGGGCCGC GCTCCCAAGG GGTGTTTCTG     360

GCACACTACG GACACGCGTG GCGCGAGCAG AGGCGCTTCT CCGTGTCCAC CTTGCGCAAC     420

TTGGGCCTGG GCAAGAAGTC CCTGGAGCGG TGGGTGACCG AGGAGGCCGC CTGCCTCTGT     480

GCCGCCTTCG CCGACCAAGC CAGACGCCCC TTTCACCCCA ACGGCCTCCT GAACAAAGCG     540

GCGAGCAACG TGATCGCCTC CCTCACCTGC GGGTGCCGCT TCGAGTACGA CGACCCTCGC     600

TTCCTCAGGC TACTGGACCT AGCTCAGAAG GGATTGAAGG AGGAGCTGGG CTTTCTGTGA     660

GAGATATGCT GAATGTTGTC CCCCTCCTCC TGCGCATCCC AGGGCTGGCT GGCAAGGTCC     720

TACGCTCCCA AAAGGCTTTC CTGACCCAGC TGGATGAGCT GCTGACCGAG CACAGAATGA     780

TCTGGGACCC AGCCTAGCCA CCCCGAGACC TGACTGAGGC CTTCCTGGCA GAGAAGGAGA     840

AGGCCAAGGG GAACCCTGAG AGCAGCTTCA ATGATGAGAA CCTGCGCATG GTGGTGGCTG     900

ACCTGTTCTT TGCCGGGATG GTGACCACCT CGATCACGCT GGCCTGGGGC CTCCTGCTCA     960

TGATCCTACG CCCCGGATGT GCAGCGCCGTG TCCAACAGAT CGACAACGTG ATAGGGCAGG    1020

TGTGGTGACC AGAGATGGGT GACCAGGCTC GCATGCCCTG CACCACTGCC GTGATTCACG    1080

AGGTGCAGCG CTTTGGGGAC ATCGTCCCCC TGGGTGTGAC CCATATGACA TCCCGTGACA    1140

TCGAAGTACA GGGCTTCCGC ATCCCTAAGG GATGATGCTC TTCACCAACC TGTCATCGGT    1200

GCTGAAGGAT GAGGCCGTCT GGAAGAAGCC CTTCCGCTTC CACCCCGAAC ACTTCCTGGA    1260

TGCCCAGGGC CACTTTGTGA AGCCGGAGGC CTTCCTGCCT TTCTCAGCAG GCCGCCGTGC    1320

ATGCCTCGGG CCAGCCCCTG GCCCGCATAG AGCTCTTCCT CTTCTTCACC TCCCTGCTGC    1380

AGCACTTCAG CTTCTCGGTG CCCACCGGAC AGCCCCGGCC CAGCCACTCT CGTGTCGTCG    1440

GCTTTCTGGT GACGCCATCC CCCTATGAGC TTTGTGCTGT GCCCCGCTAG AGTTGCTCCT    1500

C                                                                   1501
```

(2) INFORMATION FOR SEQ ID NO:25:

(i) SEQUENCE CHARACTERISTICS:
        (A) LENGTH: 13 base pairs
        (B) TYPE: nucleic acid
        (C) STRANDEDNESS: single -continued

```
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:25:

CCCCCAGGAC GCC                                                              13
```